(12) United States Patent
Molero Leon et al.

(10) Patent No.: US 12,322,508 B2
(45) Date of Patent: Jun. 3, 2025

(54) INTELLIGENT WORKFLOW ANALYSIS FOR TREATMENTS USING EXPOSABLE CLOUD-BASED REGISTRIES

(71) Applicant: Hoffmann-La Roche Inc., Little Falls, NJ (US)

(72) Inventors: Silvia Elena Molero Leon, Heredia (CR); Helene Jeanne Sahri, Basel (CH); Turap Tasoglu, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 254 days.

(21) Appl. No.: 17/926,331

(22) PCT Filed: May 19, 2021

(86) PCT No.: PCT/US2021/033048
§ 371 (c)(1),
(2) Date: Nov. 18, 2022

(87) PCT Pub. No.: WO2021/236702
PCT Pub. Date: Nov. 25, 2021

(65) Prior Publication Data
US 2023/0197271 A1    Jun. 22, 2023

(30) Foreign Application Priority Data

May 20, 2020   (EP) ..................................... 20175829
Dec. 3, 2020   (EP) ..................................... 20211596

(51) Int. Cl.
*G16H 50/20*   (2018.01)
*G16H 15/00*   (2018.01)
*G16H 20/00*   (2018.01)

(52) U.S. Cl.
CPC ............. *G16H 50/20* (2018.01); *G16H 15/00* (2018.01); *G16H 20/00* (2018.01)

(58) Field of Classification Search
CPC ........ G16H 50/20; G16H 15/00; G16H 20/00; G16H 30/40; G16H 70/60; G16H 70/20; G16H 50/70; G16H 80/00
See application file for complete search history.

(56) References Cited

U.S. PATENT DOCUMENTS 10,510,449 B1 * 12/2019 Reicher ................... G16H 15/00
2018/0196873 A1 *  7/2018 Yerebakan ............... G06N 3/08
(Continued)

FOREIGN PATENT DOCUMENTS

| CN | 111008957 A | 4/2020 |
| JP | 2012-198846 | 10/2012 |

(Continued)

OTHER PUBLICATIONS

EPO, International Search Report for International Patent Application No. PCT/US2021/033048, Aug. 25, 2021, 5 pages.
(Continued)

*Primary Examiner* — Chinyere Mpamugo
(74) *Attorney, Agent, or Firm* — IP Spring

(57) ABSTRACT

Disclosed are systems and methods for building and using a data platform to perform intelligent treatment selection to assist in clinical decision making. The present disclosure relates to a server configured to transform a subject record, which characterizes various non-numerical features of a subject, into a transformed representation that is consumable by machine-learning or artificial intelligence models. The output of the machine-learning or artificial-intelligence models can be evaluated to enable the intelligent treatment selection and other enhanced analyses, such as, for example, automatically detecting and defining subject populations, predicting treatment protocols with likely positive responsiveness, and identifying the similarity or dissimilarity between subject records along one or more dimensions.

15 Claims, 6 Drawing Sheets

(56) References Cited

U.S. PATENT DOCUMENTS

2019/0287686 A1   9/2019   Takeda
2020/0075141 A1   3/2020   Iwamura et al.

FOREIGN PATENT DOCUMENTS

| JP | 2015-524112 | 8/2015 |
| WO | 2007056601 A2 | 5/2007 |
| WO | 2013/182904 | 12/2013 |
| WO | 2019182508 A1 | 9/2019 |

OTHER PUBLICATIONS

EPO, Written Opinion for International Patent Application No. PCT/US2021/033048, Aug. 25, 2021, 8 pages.
Anonymous, "Click-to-call—Wikipedia," retrieved from Internet: https://en.wikipedia.org/w/index.php?title=Click-to-call&oldid=938120488, Jan. 29, 2020, 5 pages.
EPO, Communication pursuant to Article 94(3) EPC for European Patent Application No. 21730076.3, Feb. 9, 2024, 10 pages.
JPO, Notice of Rejection (with English translation) for Japanese Patent Application No. 2022-570469, Jan. 23, 2024, 26 pages.

\* cited by examiner

INTELLIGENT WORKFLOW ANALYSIS FOR TREATMENTS USING EXPOSABLE CLOUD-BASED REGISTRIES

CROSS-REFERENCE TO RELATED APPLICATIONS

This application is a U.S. National Stage filing under 35 U.S.C. § 371 of International Patent Application No. PCT/US2021/033048, filed May 19, 2021, which in turn claims priority under PCT Article 8 and/or 35 U.S.C. § 119 (a) to and the benefit of European Patent Application Number EP20175829.9, filed on May 20, 2020, and to European Patent Application Number EP20211596.0, filed on Dec. 3, 2020. The disclosures of European Patent Application Number EP20175829.9, European Patent Application Number EP20211596.0, and International Patent Application No. PCT/US2021/033048 are hereby incorporated by reference herein in their entirety for all purposes.

FIELD

Methods and systems disclosed herein relate generally to executing machine-learning and artificial-intelligence models using subject records to enable intelligent treatment selection and other enhanced analyses. More particularly, the present disclosure relates to a server configured to transform a subject record, which characterizes various non-numerical features of a subject, into a transformed representation (e.g., a numerical representation, such as an N-dimensional matrix or vector) that is consumable by machine-learning or artificial intelligence models. The output of the machine-learning or artificial-intelligence models can be evaluated to enable the intelligent treatment selection and other enhanced analyses, such as, for example, automatically detecting and defining subject populations, predicting treatment protocols with likely positive responsiveness, and identifying the similarity or dissimilarity between subject records along one or more dimensions.

BACKGROUND

A subject record is a digital set of data elements that characterize a subject associated with an entity, such as a medical facility. The set of data elements contained in a subject record can represent a complex combination of any number of attributes or characteristics of the subject. For example, a subject record may include a first data element, a second data element, and a third data element. The first data element may include a unique code that represents a condition that the subject has developed (e.g., a diagnostic code); the second data element may include a longitudinal series of data (e.g., vitals) collected from the subject at various intervals over a period of time (e.g., years); and the third data element may include Magnetic Resonance Images of the subject's brain. Thus, the values of data elements across the set of data elements may be in different data formats and may be of different data types.

While a subject record is configured to characterize various attributes or characteristics of a subject, this is problematic when subject records are analyzed using algorithmic techniques. Gaining analytical insights into a single subject record or into a comparison of multiple subject records is computationally problematic, given the different data formats and data types that exist in across subject records. Indeed, the different data formats and data types within each subject record constrain the ability for the subject records to be processed (e.g., inputted for processing) using analytical techniques, making it problematic to, for example, algorithmically identify subject records that are similar to a given subject record. Further, simplistic techniques such as analyzing values of a data element across multiple subject records in a time or frequency domain become computationally impractical as the pool of subject records reaches a Big-Data scale and the complexity of each individual subject record increases. Consequentially, it may be difficult to impossible to use a big data set to detect which subject record(s) correspond to a particular issue affecting a particular subject. Accordingly, a care provider may proceed to care for the particular subject without utilizing the big data and/or by merely relying on high-level studies that have some relation to the particular issue.

US 2020/0075141 discloses a medical information management apparatus that is configured to process requests to search stored medical information. A request includes a key and value that indicates a particular an item of interest and corresponding contents (e.g., disease: lung cancer). Medical information is retrieved based on the request, and a matching rate is defined to be a portion of the retrieved medical information that has a key-value pair that matches the key and value in the request. It is determined that the value is idiosyncratic information when the matching rate is equal to or less than a threshold set. For example, lung cancer may be deemed to be idiosyncratic information when it is identified as a diagnosed disease in only 0.01% of the medical information. In some contexts, it may be important that particular individuals represented in a data set not be identifiable. Accordingly, upon identifying idiosyncratic information, the information may be obscured or anonymized.

U.S. Pat. No. 10,510,669 discloses expert opinion crowdsourcing. A submitter (e.g., a patient, insurance company, law firm, etc.) may submit a medical case (e.g., an exam) to a computing system and request feedback. The computing system may match the request to an expert who may provide an opinion from his/her device. The opinion may be returned to the submitter.

"Click-to-call—Wikipedia", 29 Jan. 2020, XP055786480, [retrieved on 2021 Mar. 16] discloses a click-to-call action, where a user clicks or presses a link on a computer, smart phone, etc., and a call is facilitated. When the link is clicked on a computer, the click may trigger one or more actions that result in an entity calling the user. When the link is clicked on a device with cellular capabilities, the click may trigger dialing a number associated with the link.

WO 2007/056601 discloses representing individual documents as a vector that identifies an occurrence of each of multiple terms. The similarity of multiple documents can then be measured by the cosine coefficients, and the documents may be clustered. Each term can also be represented as a vector of document identifiers, such that association between terms can be identified. The vector representation of terms may be used to identify associations between symptoms and structures.

WO 2019/182508 discloses that a word (provided in response to a question) can be transformed into a semantic representation vector. The vector may then be compared to a predetermined semantic representation of a state associated with a mental illness or psychiatric disorder to provide a diagnosis.

CN 111 008 957 discloses using a neural network to extract features of a medical image. The features are converted into a feature vector, which is then spliced and used to obtain a classification result.

Therefore, there is still a need for technical solutions that could generate analytical insights from existing subject records to enhance the level of care provided to subjects by a care provider.

SUMMARY

In some embodiments, a computer-implemented method for performing a clinical assessment for a subject is provided. The computer-implemented method can include receiving, at a computing system and from a user device, a set of attributes of the subject as identified by a user using an interface. For example, the set of attributes can characterize the subject and one or more symptoms of the subject. The computer-implemented method can include generating a record for the subject. The record can indicate each of the set of attributes, and the record can include a data element containing a non-numerical value that represents a symptom of the one or more symptoms. The computer-implemented method can also include transforming the non-numerical value that represents the symptom into a transformed representation. The transformed representation can numerically represent the non-numerical value. The computer-implemented method can also include storing the record in a central data store, and receiving a request submitted via the interface to initiate a consult broadcast. The computer-implemented method can include querying the central data store using the transformed representation. Querying can include comparing the transformed representation of the non-numerical value with another transformed representation of another non-numerical value contained in another data element of another record. The computer-implemented method can include identifying a set of other records based on a result of the comparison, and identifying a set of destination addresses. Each of the set of destination addresses can be associated with a care provider for another subject associated with one or more of the set of other records. The computer-implemented method can also include generating a condensed representation of the record for the subject that omits or obscures at least some of the set of attributes. The computer-implemented method can include transmitting the condensed representation of the record with a selectable element to each of the set of destination addresses. Additionally, the computer-implemented method can include receiving, from another device corresponding to the destination address from the set of destination addresses, a communication generated upon another device selecting the selectable element. The computer-implemented method can include establishing a communication channel between the user device and the other device.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more processors to perform part or all of one or more methods disclosed herein.

Some embodiments of the present disclosure include a system including one or more processors. In some embodiments, the system includes a non-transitory computer readable storage medium containing instructions which, when executed on the one or more processors, cause the one or more processors to perform part or all of one or more methods and/or part or all of one or more processes disclosed herein. Some embodiments of the present disclosure include a computer-program product tangibly embodied in a non-transitory machine-readable storage medium, including instructions configured to cause one or more processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

Figure 1:
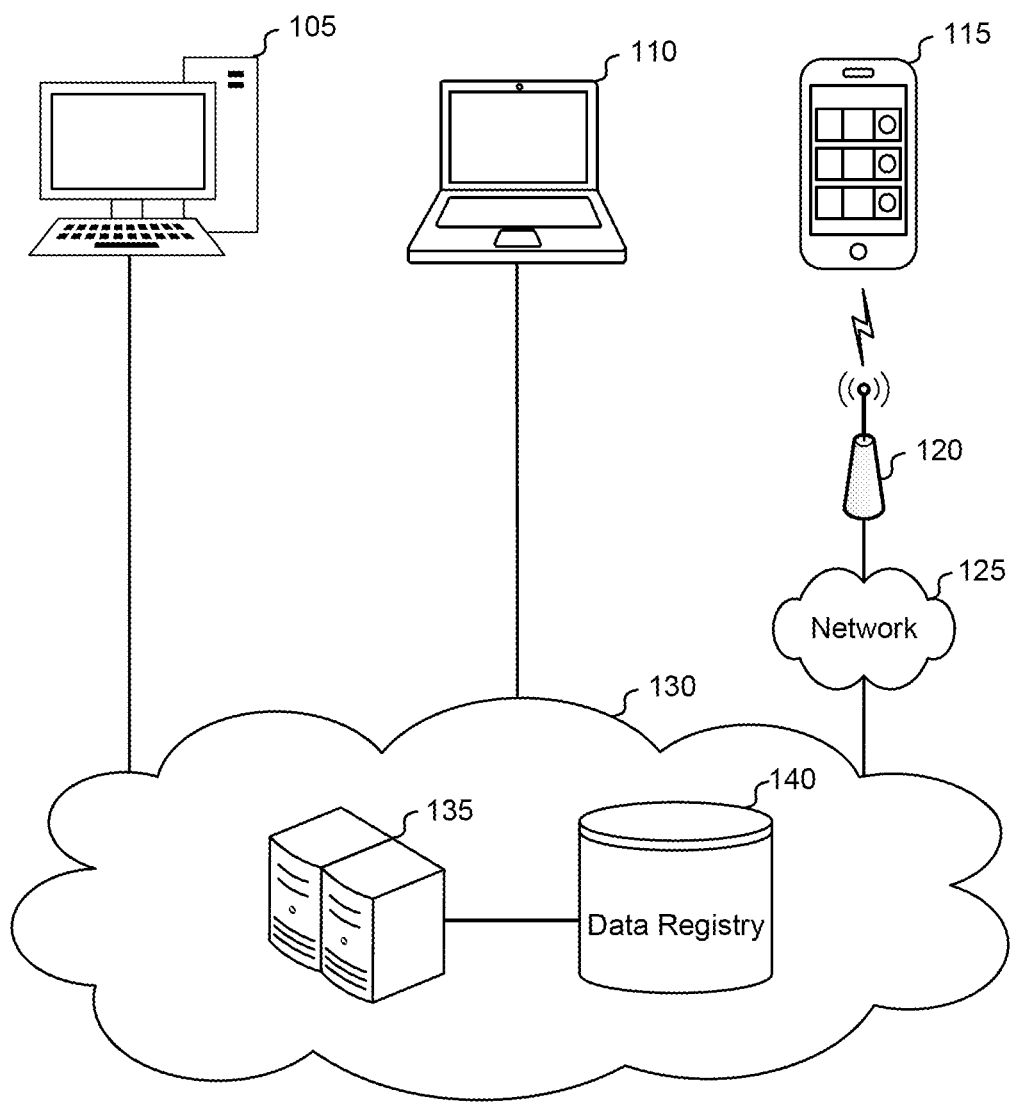
FIG. 1 illustrates a network environment in which the cloud-based application is hosted, according to some aspects of the present disclosure.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

Techniques relate to configuring a server to execute code that enables a user (e.g., a physician) of an entity to execute machine-learning or artificial-intelligence techniques using subject records. Subject records include a complex combination of data elements that characterize subjects. As an illustrative example, a subject record may include a combination of thousands of data fields. Some data fields may contain fixed non-numerical values (e.g., a subject's ethnicity), other data fields may contain unstructured text data (e.g., notes prepared by a physician), other data fields may include a time-variant series of collected measurements (e.g., glycosylated hemoglobin measurements taken two to four times a year), and other data fields may include images (e.g., MRI of a subject's brain). The complexity and variance of data types and formats in subject records make processing subject records technically challenging, if not impossible, because machine-learning and artificial-intelligence models are often configured to process data in numerical or vector form. In light of this objective technical problem, certain aspects and features of the present disclosure relate to transforming subject records into transformed representations, such as vector representations, that characterize the various data elements of the subject records.

Techniques relate to transforming the non-numerical values included in subject records into numerical representations (e.g., feature vectors) that can be inputted into machine-learning or artificial-intelligence models to generate predictive outputs. The server executing the code provides a technical effect, by transforming the subject records into transformed representations that are consumable by machine-learning or artificial-intelligence models. "Consumable" may refer to data that is in a format or form, which machine-learning or artificial-intelligence models are configured to process to generate predictive outputs. Machine-learning or artificial-intelligence models are not configured to process subject records (as they exist in their stored state in the data registries) due to the complex combinations of data elements in multiple different data formats and data types contained in each individual subject record. To illustrate, for a given subject record, a data element may include a longitudinal sequence of events (e.g., an immunization record), another data element may include measurements taken from a subject (e.g., vitals), yet another data element may include text entered by the user (e.g., notes taken by the physician), and yet another data element may be an image (e.g., an X-ray). A limited or simplistic analysis may be performed on subject records (before any transformations), such as grouping subjects based on a value of a data element (e.g., age group). However, the limited or simplistic analysis becomes problematic or infeasible as the complexity and size of subject records reaches a Big-Data scale. To process and extract analytical assessments from the subject records at a Big-Data scale, machine-learning or artificial-intelligence techniques can be used for data mining the subject records. Machine-learning or artificial intelligence models, however, are configured to receive numerical or vector inputs. For example, clustering operations, such as k-means clustering, are configured to receive numerical vectors as inputs. Thus, to perform the clustering operation on subject records, the present disclosure provides a technical effect, by transforming the subject records into transformed representations, such as numerical vector representations, that are consumable by machine-learning or artificial-intelligence models. An intelligent analysis can be performed on subject records in their transformed representation state. Non-limiting examples of intelligent analysis (performed upon the server executing code) may include automatically detecting subject groups using clustering techniques, generating outputs predictive of certain outcomes based on the values of data elements in subject records, and identifying existing subject records that are similar to a given or new subject record.

To illustrate and only as a non-limiting example, a subject record of a subject includes four data elements. The first data element contains a unique code that represents a diagnosis of a condition. The second data element contains an MRI of the subject's brain. The third data element contains a time-variant series of measurements, such as blood pressure readings, over the course of one year. The fourth data element contains unstructured notes, for example, notes of a condition detected by examining or running one or more tests. According to certain implementations, each of the first data element, the second data element, the third data element, and the fourth data element may be transformed into a transformed representation (e.g., a vector). The techniques used for transforming the values contained within the four data elements may depend on the type of data contained in a data element. For the first data element, for example, the unique code that represents a diagnosis can be represented as a fixed length vector, such that the size of the vector is determined by a size of a vocabulary of codes, and that each code in the vocabulary is represented by a vector element of the fixed length vector. The one or more unique codes contained within the first data element may be compared with the vocabulary of codes. If a unique code matches a code of the vocabulary, then a "1" may be assigned to the vector element at the position of the vector that corresponds to the unique code and a "0" may be assigned to all remaining vector elements of the vector. In light of the above, a first vector may be generated to represent the value of the first data element. As another example, for the second data element, a latent-space representation of the image may be generated using a trained auto-encoder neural network. The latent-space representation of the input image may be a reduced-dimensionality version of the input image. The trained auto-encoder neural network may include two models: an encoder model and a decoder model. The encoder model may be trained to extract a subset of salient features from the set of features detected within the image. A salient feature (e.g., a keypoint) may be a region of high intensity within the image (e.g., an edge of an object). The output of the encoder model may be a latent-space representation of the input image. The latent-space representation may be outputted by a hidden layer of the trained auto-encoder model, and thus, the latent-space representation may only be interpretable by the server. The decoder model may be trained to reconstruct the original input image from the extracted subset of salient features. The output of the encoder model may be used as the feature vector that represents the pixel values of the image included in the second data element. In light of the above, a second vector (e.g., the latent-space representation) may be generated to represent the image contained in the second data element. As another example, for the third data element, the time-variant sequence of measurements can be represented numerically. In some implementations, the time-variant sequence can be represented by a total of the instances a measurement was taken from a subject. In other implementations, the time-variant sequence can be represented numerically using an average, mean, or median of the values of the measurements taken across the instances of measurements that occurred during a time period (e.g., one year). In other implementations, a frequency of measurements can be calculated and used to numerically represent the time-variant sequence of measurements. In light of the above, a third vector may be generated to represent the time-variant sequence of values contained within the third data element. As yet another example, for the fourth data element, the notes inputted by the user may be processed and vectorized using any number of natural language processing (NLP) text vectorization techniques. In some implementations, a word-to-vector machine-learning model, such as a Word2Vec model, may be executed to transform the notes contained in the fourth data element into a single vector representation. In other implementations, a convolutional neural network may be trained to detect words or numbers within text that indicate symptoms, treatments, or diagnoses from the notes contained in the fourth data element. In light of the above, a fourth vector may be generated to represent the text of the notes contained of the fourth data element as a vector representation. Thus, the final feature vector that represents the entire subject record may be a vector of vectors, including a concatenation of the first vector, the second vector, the third vector, and the fourth vector. In other examples, an average of the first vector, the second vector, the third vector, and the fourth vector may be used to numerically represent the entire subject record. As a non-limiting example, any transformation (e.g., a linear transformation) can be performed on any one or more of the first vector, the second vector, the third vector, and so on, to ensure that each vector has the same dimensionality. Other combinations of the first vector, second vector, third vector, and fourth vector may be used to generate the final feature vector that numerically represents the entire subject record.

In some implementations, instead of generating a vector to numerically represent each data element of a subject record, techniques may be executed to reduce the dimensionality of the subject record by identifying and selecting a subset of data elements from the set of data elements. The subset of data elements may represent the "important" data elements, where "importance" of a data element is determined based on a prediction using feature extraction techniques, such as Singular Value Decomposition (SVD). For example, transforming a subject record into a transformed representation that is consumable by machine-learning and artificial-intelligence models may include performing one or more feature extraction techniques on the non-numerical values included in the data elements of a subject record to generate a feature vector that numerically represents a decomposed version of the non-numerical values. In some implementations, feature extraction techniques may include, for example, reducing the dimensionality of a set of data elements of a subject record (e.g., each data element representing a feature or dimension of a subject) into an optimal subset of features that can be used to, for example, predict an outcome or event. Reducing the dimensionality of the set of data elements may include reducing N data elements into a subset of M elements, where M is smaller than N. In these implementations, each element of the subset of M elements may be transformed into a numerical value. In some implementations, a feature vector may be generated to represent the N data elements of a subject record. The feature vector may include a vector for each data element of the set of data elements. For example, the feature vector may be a numerical representation of the complex combinations of data elements of a subject record. Each non-numerical value in a data element of a subject record can be vectorized to generate a representative vector. The vectors representing the set of data elements in a subject record may be concatenated or combined (e.g., as an average or weighted average) to generate the feature vector that numerically characterizes the entire set of data elements of the subject record. The feature vector is consumable by a trained machine-learning or artificial-intelligence model. Once the feature vector for a subject record is generated, the subject record can be evaluated individually or in groups of other subject records using machine-learning and artificial-intelligence techniques. After the feature vector that represents each subject record has been generated and stored, the feature vectors of the subject records stored in a central data store can be inputted into machine-learning or artificial-intelligence models or other enhanced analyses can be performed on the numerical representations of the subject records. For example, two different subject records can be compared with respect to one or more dimensions. A dimension may represent a feature or data element of a subject record, along which a comparison between two or more subject records is made. To illustrate, a data element of a first subject record contains text inputted by a first user (e.g., doctor) describing symptoms of a first subject. The text (e.g., the value of the data element of the first subject record) can be vectorized using the text vectorization techniques (e.g., Word2Vec) described above to generate a first vector to numerically represent the text associated with the data element. The text vectorization technique may generate an N-dimensional word vector for each word included in the text. The matching data element of a second subject record (e.g., the data element of another subject record that also contains text inputted by a physician describing symptoms of another subject) may contain text inputted by a second user describing the symptoms of a second subject. The text (e.g., the value of the data element of the second subject record) can be vectorized using the text vectorization techniques described above to generate a second vector (e.g., an N-dimension word vector) to represent the text associated with the data element. A server may compare the first vector with the second vector in a Euclidean or cosine space to quantify a similarity or dissimilarity between the first subject record and the second subject record at least with respect to the dimension of a subject's presentation of symptoms. If the first vector and the second vector are near each other (or within a threshold distance) in the Euclidean space (e.g., if the Euclidean distance between the first vector and the second vector is small), then the symptoms experienced by the first subject (as described in the text of the data element) are likely similar to the symptoms experienced by the second subject (as described in the text of the data elements). However, if the Euclidean distance between the first vector and the second vector is large or above the threshold distance (e.g., or if the Euclidean distance is above a threshold), then the symptoms experienced by the first subject can be predicted to be different from the symptoms experienced by the second subject.

In some implementations, a server may be configured to execute an application that enables a user of an entity to build data registries that serve to store subject records for subsequent processing. The data of a subject record may include unstructured data, such as electronic copies of physician notes and/or responses to open-ended questions. The unstructured data can be ingested into the data registries by mapping portions of the unstructured data to fixed parts (e.g., data elements) of structured data records. Fixed parts of structured data records may refer to data elements that contain data corresponding to a predetermined type of unstructured data (e.g. physician notes, response to specific questions, a type of images or vitals, etc.) and/or to predetermined values that can be associated with unstructured data (e.g. a set of possible symptoms that may be described in unstructured data, a set of possible conditions, etc.) The structure of the structured data records may be defined using (for example) specifications from a module that corresponds to a particular use case (e.g., particular disease, particular trial, etc.). For example, each word of the unstructured note data (e.g., text) may be transformed into a numerical representation and the various numerical representations associated with the unstructured note data can be decomposed (e.g., using SVD) to detect words describing a particular set of symptoms that the subject has exhibited. The decomposition of the numerical representations of the unstructured note data may remove non-informative words, such as "and," "the," "or," and so on. The remaining words represent the particular set of symptoms. Some portions of the note data may be irrelevant with regard to data elements in the structured data and/or may be more or less specific than data contained in data elements. In some instances, various mapping (e.g., mapping a "poor balance" symptom to a "neurological" symptom), natural-language-processing, or interface-based approach (e.g., that requests new information from a user) can be used to obtain structured data records. An interface may also be used to receive input that identifies new information about a new or existing subject, and the interface may include input components and selection options that map to a structure of data records.

Further, techniques relate to configuring a cloud-based application to transform non-numerical values contained in data elements of subject records into numerical representations, so that the cloud-based application can execute intelligent analytical functionality using the numerical representations (e.g., the transformed representations) of the subject records stored in the data registries. The transformation of non-numerical values of data elements of subject records to numerical representations may be dependent on the type of data contained in a data element. For example, for data elements that include text, such as notes taken by a user, the text may be transformed into numerical representations of the text using natural language processing techniques, such as Word2Vec or other text vectorization techniques. As another example, for data elements that include images (e.g., Mills) or image frames of a video (e.g., a video of an ultrasound), each image or image frame may be transformed into a numerical representation (e.g., vector) using a trained auto-encoder neural network, which is trained to generate a latent-space representation of an input image. The condensed representation of the input image (e.g., the latent-space representation) may serve as the vector that numerically represents the input image. As yet another example, for data elements that include a time-variant sequence of information (e.g., events occurring over a period of time), the time-variant information can be represented as a numerical representation using several exemplary transformations. In some instances, the count of events may be used as the vector representing the time-variant information. In other instances, the frequency or rate of events occurring (e.g., per week, per month, per year, etc.) may be used as the vector representing the time-variant information. In still other instances, an average or combination of the measurement values associated with each event in the time-variant information can be used as the vector representing the time-variant information. The present disclosure is not limited to these examples, and thus, other numerical representations of time-variant information can be used as the vector that represents the numerical representation. Intelligent analytical functionality may be performed by executing trained machine-learning or artificial-intelligence models using data records. The model outputs may be used to indicate certain analytics extracted from the data records.

Additionally, techniques disclosed herein relate to configuring a cloud-based application to execute data-privacy protocols that enable an entity to transmit and/or receive one or more data records or other information characterizing subjects (e.g., experiencing medical symptoms and/or having a possible or confirmed diagnosis of a medical condition) with external entities, while satisfying the constraints imposed by data-privacy rules across various jurisdictions. The cloud-based application can be configured to algorithmically assess data-privacy violations and automatically omit, obfuscate or otherwise modify data records to comply with data-privacy rules. These techniques may be performed in combination with any technique described herein.

In some instances, transmission of data from a subject record may be provided to develop a treatment plan for an individual subject. For example, subject-record information (e.g., that complies with data-privacy restrictions via, for example, select omission and/or obscuring of data) may be broadcast and/or transmitted to a select group of user devices. For example, a broadcast may be transmitted to user devices associated with similar data records in response to input from the user corresponding to a request to initiate a consult with a user associated with a similar subject. If a user receiving the broadcast accepts a consultation request (via provision of corresponding input), a secure data channel may be established between the user and potentially more of the subject record may be shared (e.g., while conforming to data-privacy restrictions applicable to the two users). Subject records that are similar to a given subject may be identified by performing a nearest-neighbor technique using the vector representations of two or more subject records. Nearest neighbor techniques may be performed by comparing vectors of individual data elements across multiple subject records (e.g., the nearest neighbor may be determined in association with a dimension or feature of the subject records). When vectors of individual data elements are compared, the individual elements may be matching data elements, such as vectors corresponding to a first (resp., second, third, etc.) data element or first (resp. second, third, etc.) type of data element, where a type can refer to, for example, free text notes, images, images from a specific imaging modality, time-series, vitals, etc. Alternatively, the nearest neighbor techniques may be performed by comparing the overall vector that characterizes the entire subject record with the overall vector that characterizes another entire subject record. An overall vector may be a concatenation of individual vectors representing the values of the data elements, or may be an average or combination of the individual vectors representing the values of the data elements.

As another example, one or more processed data records may be returned in response to a query for subject records matching particular constraints. In some instances, a first user may submit a query that identifies a first subject record. The query may correspond to a request to identify other subject records that are similar to the first subject record. A server may transform the first subject record into a transformed representation using certain transformation techniques, discussed above and herein. Alternatively, the transformed representation of the first subject record may have previously been generated and stored in a database. Regardless of whether the transformed representation of the first subject record is generated before or after the query is received, transforming the first subject record into a transformed representation of the first subject record may include generating a vectorization of one or more non-numerical values of data elements of the first subject record. Vectorizing the one or more non-numerical values contained within the first subject record may include generating a numerical vector representation for each value (e.g., for non-numerical text, such as notes) included in each data element of the first subject record. The various vector representations may be concatenated or otherwise combined (e.g., an average may be computed) to generate the feature vector that represents the entire first subject record. The vector representation that numerically represents the first subject record may be compared in a domain space (e.g., Euclidean space or cosine space) to vector representations of other subject records. When the Euclidean distance, for example, between two vector representations is within a threshold distance, then the two subject records associated with the two vector representations may be interpreted (e.g., by a server) as being similar at least with respect to one or more dimensions.

For each data element in a subject record, the technique used to generate the vector representation of the value associated with the data element may depend on the type of data associated with the data element. In some examples, the data element of a subject record may be associated with one or more images, such as X-rays of the subject. Feature extraction techniques may be executed to generate a vector representation of each image associated with the data element. For example, a server may be configured to execute a trained auto-encoder neural network to generate a reduced-dimensionality version of the image. The trained auto-encoder neural network may include two models: an encoder model and a decoder model. The encoder model may be trained to extract a subset of salient features from the set of features detected within the image. A salient feature (e.g., a keypoint) may be a region of high intensity within the image (e.g., an edge of an object). The output of the encoder model may be a latent-space representation of the input image. The latent-space representation may be outputted by a hidden layer of the trained auto-encoder model, and thus, the latent-space representation may only be interpretable by the server. The subset of salient features of the latent-space representation that characterizes the subject record can be compared against the subset of salient features of the latent-space representation that characterizes another subject record to yield certain analytical insights. The decoder model may be trained to reconstruct the original input image from the extract subset of salient features. The output of the encoder model may be the vector representation of the data element associated with the image included the subject record. In other examples, keypoint matching techniques (e.g., techniques that compare a set of pixels detected as a keypoint in one image to a different set of pixels detected as a keypoint in another image) may be executed to match keypoints of an image contained in a data element of a first subject record to keypoints of another image contained in a data element of a second subject record. The vector representation (e.g., the latent-space representation) of the input image is consumable by machine-learning or artificial-intelligence models, and thus, two different subject records (each including an image) may be compared against each other to determine a similarity or a dissimilarity between the two different subject records.

To illustrate and only as a non-limiting example, a magnetic resonance image (MRI) of a subject's brain is captured. The MRI is stored in the subject record associated with the subject. The server is configured to generate a transformed representation, such as a vector representation, of the MRI contained in the subject record using feature extraction techniques, such as keypoint detection, auto-encoding to latent-space representations, SVD, and other suitable computer-vision techniques. The vector representation of the data element that contains the MRI is concatenated or otherwise combined (e.g., averaged) with the vector representations of some or all of the remaining data element of the set of data elements to generate the feature vector that characterizes the entire subject record. A user may access an application to query a database of other subject records to retrieve a set of subset other subject records that contain MRIs that are similar to the MRI of the subject's brain. Identifying other subject records that are similar to the subject record (at least with respect to similarity between MRIs) may involve calculating the k-nearest neighbors of the subject record. For example, the transformed representation may be plotted (visually or internally by a computing system) on a domain space, such as a Euclidean space or cosine space. The transformed representation of each other subject record may also be plotted (visually or internally by a computing system). A nearest-neighbor technique may be executed to compare the vector representation of the subject record with the vector representations of the other subject records to identify the k nearest neighbors to the subject vector. The k nearest neighbors that are identified may be predicted to have MRIs that are similar to the MM of the subject's brain. Each other subject record that is identified as a nearest neighbor may be identified and retrieved for further evaluation or processing using the application.

In some implementations, a computing system may perform a data-processing technique (e.g., nearest-neighbor technique) to identify similar subject records. Various data elements may be differentially weighted in this search (e.g., in accordance with predefined data element weightings, user input that indicates an importance of matching various data elements, and/or a prevalence of particular data element values across a subject record set). When searching across a set of records for potential matches, some records may lack values for various data elements. In these cases, it may be determined that (for example) the data element values do not match and/or the data element may be unweighted when evaluating the potential match. Handling of the missing-value may depend on a distribution of values for the data element across the set of records and/or the value for the data element in the query.

Further, some techniques relate to defining and using a set of rules used to identify potential treatment regimens for a subject given a set of symptoms identified in the subject record. To illustrate, a target subject record may represent a target subject who recently experienced three symptoms: an upper respiratory infection, a fever, and a sore throat. The three symptoms may be written as text within a data element of the target subject record (e.g., the separation between words being marked by a tag, such as a semicolon). A server, such as cloud server 135, may individually input the text "upper respiratory infection," "fever," and "sore throat" into a trained Word2Vec model or other text-to-vector model, such as vocabulary mapping. The Word2Vec model may be trained to generate a vector representation for each word that represents a symptom. The vector representations for the three symptoms may be averaged (or concatenated or otherwise combined, as explained above) to generate a single vector representation for the "symptoms" data element of the target subject record. The single vector representation for the "symptoms" data element of the target subject record may be processed to identify other subject records that include similar words in the "symptoms" data element. Each subject record stored in the database may be associated with an existing "symptoms" data element that has been transformed into a numerical representation, such as a vector. The vector for the "symptoms" data element may be plotted and compared against the vector for the "symptoms" data element of the target subject record. The server may identify the nearest vector to the vector characterizing the "symptoms" data element. The vector of the "symptoms" data element nearest the vector of the target subject record may be predicted to be similar to the subject. The subject record associated with the nearest vector to the vector of the target subject record may be identified and further evaluated to determine the treatment regimen provided to that subject. The treatments that were provided to the subject associated with the vector nearest the vector for the target subject record may be used as potential treatment regimens to treat the target subject. Additionally, each potential treatment regimen may be weighted by the responsiveness experienced by the other subject. The potential treatment regimens may be sorted according to the responsiveness that the other subject experienced.

A set of rules may be defined based on a user interaction with a user interface, which may include specifications of particular criteria and an associated particular medical treatment and/or selection of one or more previously defined rules (that specify criteria and a treatment). For example, one or more existing rules may be presented via an interface, and a user may select rules to incorporate into a rule-base associated with an account associated with the user. The one or more rules may be selected from amongst a set of rules defined by multiple users (e.g., associated with one or more institutions) and/or may be generated based on rules generated by multiple users. When a user selects a rule for incorporating into a rule-base, the application may generate a feedback signal to cloud server 135. The feedback signal may include metadata associated with the user's selection. The metadata may indicate whether the rule was incorporated into the rule-base without modification or with modification. If the rule-base was modified, then the metadata would indicate which modification was made to the rule. The metadata may also indicate whether or not the rule was rejected, deleted, or otherwise determined not to be useful to the user. To illustrate and as a non-limiting example, a computing system may detect that rules that relate one or more particular types of symptoms and/or test results to a given treatment are relatively frequently defined and/or selected by users, and the computing system may then generate a general rule pertaining to the particular types of symptoms and/or test results and to the treatment. The general rule may be defined to have (for example) a most restrictive, most inclusive or median criteria. In some instances, a rule base of a user can be processed to detect any criteria overlap between rules. Upon identifying an overlap, an alert may be presented that identifies the overlap. A rule of a rule base may be used to evaluate a subject record to define a population associated with the subject record (e.g. by classification). Evaluating the subject record using the rule may be performed as a decision tree, for example, in that a first criterion of the rule is compared against the attributes included in the subject record. If the first criterion is satisfied, then the next criterion is compared against the attributes included in the subject record. If the next criterion is satisfied, then the comparisons continue for each criterion included in the rule. The comparisons may continue even if the next criterion is not satisfied. In this case, the non-satisfaction of the criterion (and any others included in the rule) is stored and presented to a user device, along with the criteria that were satisfied.

Further, embodiments of the present disclosure provide a cloud-based application configured to exchange subject information with external entities without violating data-privacy rules. The cloud-based application is configured to automatically assess data-privacy rules involved in sharing subject information across various jurisdictions. The cloud-based application is configured to execute protocols that obfuscate or otherwise modify the subject information, thereby algorithmically ensuring compliance with the data-privacy rules.

II. Network Environment for Hosting the Cloud-Based Application Configured with Intelligent Functionality FIG. 1 illustrates network environment 100, in which an embodiment of the cloud-based application is hosted. Network environment 100 may include cloud network 130, which includes cloud server 135 and data registry 140. Cloud server 135 may execute the source code underlying the cloud-based application. Data registry 140 may store the data records ingested from or identified using one or more user devices, such as computer 105, laptop 110, and mobile device 115.

The data records stored in data registry 140 may be structured according to a skeleton structure of fixed parts (e.g., data elements). Computer 105, laptop 110, and mobile device 115 may each be operated by various users. For example, computer 105 may be operated by a physician, laptop 110 may be operated by an administrator of an entity, and mobile device 115 may be operated by a subject. Mobile device 115 may connect to cloud network 130 using gateway 120 and network 125. In some examples, each of computer 105, laptop 110, and mobile device 115 are associated with the same entity (e.g., the same hospital). In other examples, computer 105, laptop 110, and mobile device are associated with different entities (e.g., different hospitals). The user devices of computer 105, laptop 110, and mobile device 115 are examples for the purpose of illustration, and thus, the present disclosure is not limited thereto. Network environment 100 may include any number or configuration of user devices of any device type.

In some embodiments, cloud server 135 may obtain data (e.g., subject records) for storing in data registry 140 by interacting with any of computer 105, laptop 110, or mobile device 115. For example, computer 105 interacts with cloud server 135 by using an interface to select subject records or other data records stored locally (e.g., stored in a network local to computer 105) for ingesting into data registry 140. As another example, computer 105 interacts with an interface to provide cloud server 135 with an address (e.g., a network location) of a database storing subject records or other data records. Cloud server 135 then retrieves the data records from the database and ingests the data records into data registry 140.

In some embodiments, computer 105, laptop 110, and mobile device 115 are associated with different entities (e.g., medical centers). The data records that cloud server 135 obtains from computer 105, laptop 110, and mobile device 115 may be stored in different data registries. While the data records from each of computer 105, laptop 110, and mobile device 115 may be stored within cloud network 130, the data records are not intermingled. For example, computer 105 cannot access the data records obtained from laptop 110 due to the constraints imposed by data-privacy rules. However, cloud server 135 may be configured to automatically obfuscate, obscure, or mask portions of the data records when those data records are queried by a different entity. Thus, the data records ingested from an entity may be exposed to a different entity in an obfuscated, obscured, or masked form to comply with data-privacy rules.

Once the data records are collected from computer 105, laptop 110, and mobile device 115, the data records may be used as training data to train machine-learning or artificial-intelligence models to provide the intelligent analytical functionality described herein. The data records may also be available for querying by any entity, given that when a user device associated with an entity queries data registry 140 and the query results include data records originating from a different entity, those data records may be provided or exposed to the user device in an obfuscated form, which complies with data-privacy rules.

Cloud server 135 may be configured in a specialized manner to execute code that, when executed, causes intelligent functionality to be performed using transformed representations of subject records (e.g., a vector that numerically represent the information stored in a subject record). For example, intelligent functionality may be performed by executing code using cloud server 135. The executed code may represent a trained neural network model. The neural network model may have been trained to perform intelligent functions, such as predicting a subject's responsiveness to a treatment regimen, identifying similar patients, generating a recommendation of a treatment regimen for a patient, and other intelligent functionality. The neural network model may be trained using a training data set that includes subject records of subjects who have previously been treated for a condition and experienced an outcome (e.g., overcoming a condition, increasing a severity of a condition, reducing a severity of a condition, and so on). Additionally, the executed code may be configured to cause cloud server 135 to transform non-numerical values of existing subject records into numerical representations (e.g., a transformed representation), which can be processed by the trained neural network model. For example, the code executed by cloud server 135 can be configured to receive as input each subject record of a set of subject records, and for each subject record, the code, when executed, can cause cloud server 135 to perform the operations described herein for transforming each data element of each subject record into a transformed representation, such as a vector representation. Executing intelligent functionality may include inputting at least a portion of the data records stored in data registry 140 into a trained machine-learning or artificial-intelligence models to generate outputs for further analysis. In some embodiments, the outputs can be used to extract patterns within the data records or to predict values or outcomes associated with data fields of the data records. Various embodiments of the intelligent functionality executed by cloud server 135 are described below.

In some embodiments, cloud server 135 is configured to enable a user device (e.g., operated by a doctor) to access the cloud-based application to transmit consult broadcasts to a set of destination devices. A consult broadcast may be a request for support or assistance regarding the treatment of a subject associated with a subject record. A destination device may be a user device operated by another user associated with another entity (e.g., a doctor at another medical center). If a destination device accepts the request for assistance associated with the consult broadcast, the cloud-based application may generate a condensed representation of the subject record that omits or obscures certain data fields of the subject record. The condensed representation may comply with data-privacy rules, and thus, the condensed representation of the subject record cannot be used to uniquely identify the subject associated by the subject record. The cloud-based application may transmit the condensed representation of the subject record to the destination device that accepted the request for assistance. The user operating the destination device may evaluate the condensed representation and communicate with the user device using a communication channel to discuss options for treating the subject. For example, the communication channel may be configured as a secure chatroom that enables the user device (e.g., operated by the doctor requesting the consult) to securely communicate with the destination device (e.g., operated by the other doctor providing the consult).

In some embodiments, cloud server 135 is configured to provide a treatment-plan definition interface to user devices. The treatment-plan definition interface enables user devices to define a treatment plan for a condition. For example, a treatment plan may be a workflow for treating a subject with the condition. A workflow may include one or more criteria for defining a population of subjects as having the condition. The workflow may also include a particular type of treatment for the condition. The cloud server 135 receives and stores treatment-plan definitions for a particular condition from each user device of a set of user devices. The cloud-based application may distribute a treatment plan for a given condition to a set of user devices. Two or more user devices of the set of user devices may be associated with different entities. Each of the two or more users devices may be provided with the option to integrate any portion or the entire treatment plan into a customer rule set. Cloud server 135 can monitor whether user devices integrate the shared treatment plan in full or integrate part of the treatment plan. The interactions between the user devices and the shared treatment plan can be used to determine whether to update the treatment plan or a rule created based on the treatment plan.

In some embodiments, cloud server 135 enables a user operating a user device to access the cloud-based application to determine a proposed treatment for a subject with a condition. The user device loads an interface associated with the cloud-based application. The interface enables the user operating the user device to select a subject record associated with a subject being treated by the user. The cloud-based application may evaluate other subject records to identify a previously-treated subject who is similar to the subject being treated by the user. The similarity between subjects, for example, may be determined using an array representation of the subject records. An array representation (e.g., a transformed representation, such as a vector, an N-dimensional matrix, or any numerical representation of a non-numerical value) may be any numerical and/or categorical representation of the values of data fields of a subject record. For example, an array representation of a subject record may be a vector representation of the subject record in a domain space, such as in a Euclidean space. In some instances, cloud server 135 may be configured to transform an entire subject record into a numerical representation, such as a vector. For a given subject record, cloud server 135 may evaluate each data element to determine the type of data contained or included in that data element. The type of data may inform the cloud server 135 as to which process or technique to perform to transform the numerical or non-numerical values of that data element into a numerical representation. As an illustrative example, cloud server 135 may transform non-numerical values (e.g., the text of a physician's notes) of a data element of a subject record into a numerical representation (e.g., a vector). The transformation may include using natural language processing techniques, such as Word2Vec or other text vectorization techniques, to generate a numerical value that represents each word of text. The generated numerical value may serve as a vector that can be inputted into a trained neural network to perform intelligent analysis. As another illustrative example, for data elements that include images (e.g., MM data) or image frames of a video (e.g., a video data of an ultrasound), each image or image frame may be transformed into a numerical representation (e.g., vector) using a trained auto-encoder neural network, which is trained to generate a latent-space representation of an input image. The condensed representation of the input image (e.g., the latent-space representation) may serve as the numerical representation of the input image. This numerical representation can be inputted into a neural network or other machine-learning model to perform intelligent analysis of the associated subject record. As yet another example, for data elements that include a time-variant sequence of information (e.g., events occurring or measurements taken from a subject over a period of time), the time-variant information can be represented as a numerical representation using several exemplary transformations. In some instances, the count of events may be used as the vector representing the time-variant information. For example, if a measurement was taken with respect to a subject four times in one year, the numerical representation may be "4." In other instances, the frequency or rate of events occurring (e.g., per week, per month, per year, etc.) may be used as the vector representing the time-variant information. In still other instances, an average or combination of the measurement values associated with each event in the time-variant information can be used as the vector representing the time-variant information. The present disclosure is not limited to these examples, and thus, other numerical representations of time-variant information can be used as the vector that represents the numerical representation.

In some instances, multiple values in an array representation correspond to a single data element. For example, a value of a data element may be represented by multiple binary values generated via one-hot encoding. As another example, each value of the multiple values in a single data element of a subject record may be individually transformed into a numerical representation, as described above. The numerical representation that represents each value of the multiple values can be combined into a single numerical representation that corresponds to the data element. Combining multiple numerical representations may be performed using any vector combination techniques, such as averaging vector magnitudes, adding vectors, or concatenating multiple vectors into a single vector. In some instances, the cloud-based application may generate array representations for each subject record of a group of subject records. Similarity between two subject records may be represented by comparing the two array representations to determine a distance between them. Subject records can also be compared along a dimension (e.g., a data element), instead of comparing a numerical representation of an entire subject record with another numerical representation of another subject record. For example, comparing two subject records along a dimension may include comparing the numerical representation of a data element of a subject record with another numerical representing of a matching data element of another subject record. Further, the cloud-based application may be configured to identify a subject who is a nearest neighbor to the subject record selected by the user device using the interface. The nearest neighbor may be determined by comparing the numerical representations of the various subject records with the numerical representation of a target subject record. The cloud-based application may identify treatments previously performed on the subject who is the nearest neighbor. The cloud-based application may avail on the interface the previously-performed treatments on the nearest neighbor.

In some embodiments, cloud server 135 is configured to create queries that search a database of previously-treated subjects. Cloud server 135 may execute the queries and retrieve subject records that satisfy the constraints of the query. In presenting the query results, however, the cloud-based application may only present the subject record in full for subjects who have been or who are being treated by the user who created the query. The cloud-based application masks or otherwise obfuscates portions of subject records for subjects who are not being treated by the user creating the query. The masking or obfuscation of portions of subject records that are included in the query results enables the user to comply with data-privacy rules. In some embodiments, the query results (regardless of whether the query results are obfuscated or not) can be automatically evaluated for patterns or common attributes within the subject records.

In some embodiments, cloud server 135 embeds a chatbot into the cloud-based application. The chatbot is configured to automatically communicate with user devices. The chatbot can communicate with a user device in a communication session, in which messages are exchanged between the user device and the chatbot. A chatbot may be configured to select answers to questions received from user devices. The chatbot may select answers from a knowledge base accessible to the cloud-based application. When a user device transmits a question to the chatbot, and that chatbot does not have a preexisting answer stored in the knowledge base, then a different representation of the question for which there is a preexisting answer stored in the knowledge base. The user communicating with the chatbot can be prompted as to whether the answer provided by the chatbot is accurate or helpful.

It will be appreciated that any machine-learning or artificial-intelligence algorithms may be executed to generate any of the trained machine-learning models described herein. Various different types and technologies of artificial-intelligence-based and machine-learning models may be trained and then executed to generate one or more outputs predictive of user outcomes for performing a protocol or function. Non-limiting examples of models include Naïve Bayes models, random forest or gradient boosting models, logistic regression models, deep learning neural networks, ensemble models, supervised learning models, unsupervised learning models, collaborative filtering models, and any other suitable machine-learning or artificial intelligence models.

It will be appreciated that the cloud-based application can be configured to perform intelligent functionality with respect to consulting external physicians, determining diagnosis and proposing treatment for any disease, condition, area of study, or disorder, including, but not limited to, COVID-19, oncology, including cancers of the lung, breast, colorectal, prostate, stomach, liver, cervix uteri (cervical), esophagus, bladder, kidney, pancreas, endometrium, oral, thyroid, brain, ovary, skin, and gall bladder; solid tumors, such as sarcomas and carcinomas, cancers of the immune system including lymphomas (such as Hodgkin or non-Hodgkin), and cancers of the blood (hematological cancers) and bone marrow, such as leukemias (such as Acute lymphocytic leukemia (ALL) and Acute myeloid leukemia (AML)), lymphomas, and myeloma. Additional disorders include blood disorders such as anemia, bleeding disorders such as hemophilia, blood clots, ophthalmology disorders, including diabetic retinopathy, glaucoma, and macular degeneration, neurological disorders, including multiple sclerosis, Parkinson's, disease, spinal muscular atrophy, Huntington's Disease, amyotrophic lateral sclerosis (ALS), and Alzheimer's Disease, autoimmune disorders, including multiple sclerosis, diabetes, systemic lupus erythematosus, myasthenia gravis, inflammatory bowel disease (IBD), psoriasis, Guillain-Barre syndrome, Chronic inflammatory demyelinating polyneuropathy (CIDP), Graves' disease, Hashimoto's thyroiditis, eczema, vasculitis, allergies and asthma.

Other diseases and disorders include but are not limited to kidney disease, liver disease, heart disease, strokes, gastrointestinal disorders such as celiac disease, Crohn's disease, diverticular disease, Irritable Bowel Syndrome (IBS), Gastroesophageal Reflux Disease (GERD) and peptic ulcer, arthritis, sexually transmitted diseases, high blood pressure, bacterial and viral infections, parasitic infections, connective tissue diseases, celiac disease, osteoporosis, diabetes, lupus, diseases of the central and peripheral nervous systems, such as Attention deficit/hyperactivity disorder (ADHD), catalepsy, encephalitis, epilepsy and seizures, peripheral neuropathy, meningitis, migraine, myelopathy, autism, bipolar disorder, and depression.

Figure 2:
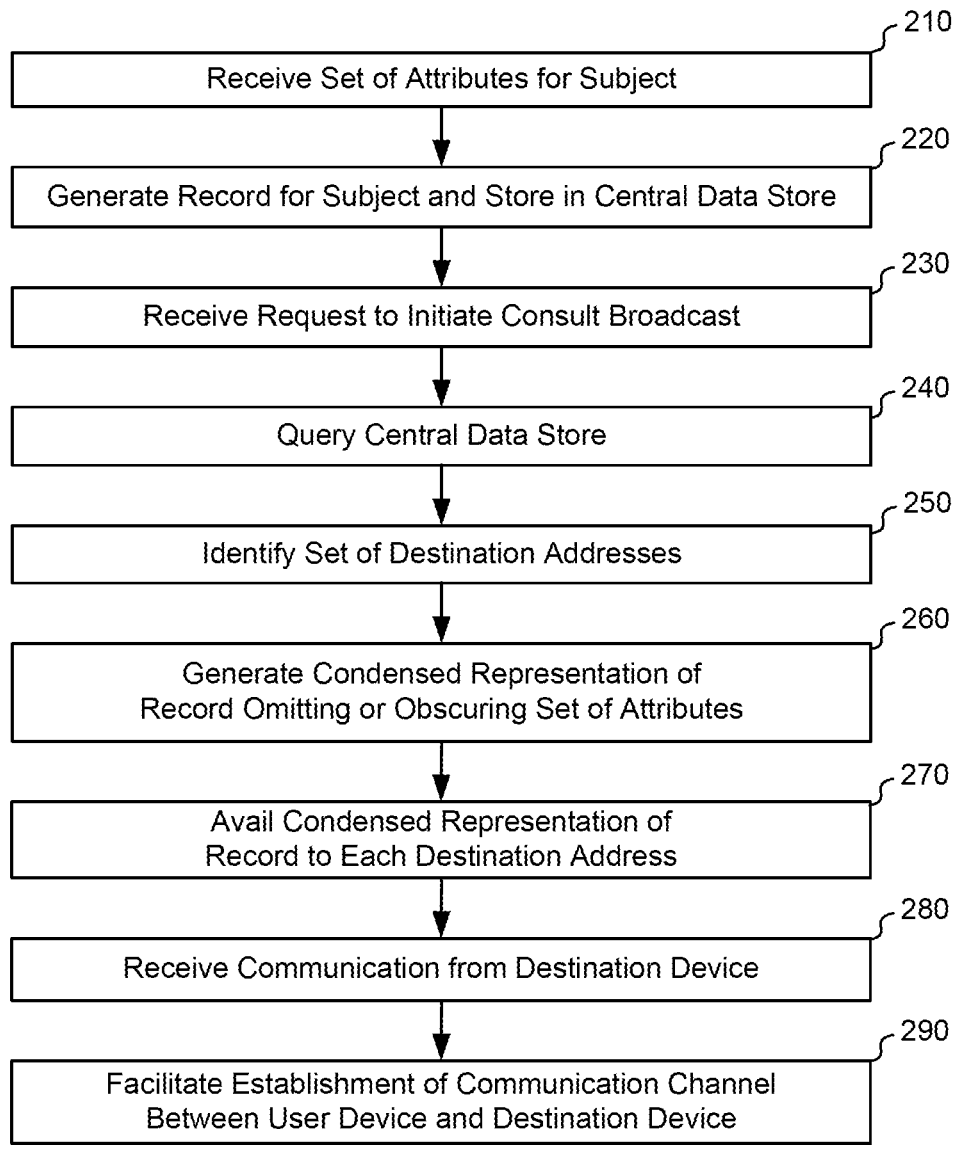
FIG. 2 is a flowchart illustrating an example of a process performed by the cloud-based application to distribute condensed subject records to user devices in association with a consult broadcast requesting assistance with treating a subject, according to some aspects of the present disclosure.

II.A. The Cloud-Based Application Enables User Devices to Broadcast Consult Requests to Other User Devices and Automatically Condenses Subject Records to Comply with Data-Privacy Rules FIG. 2 is a flowchart illustrating process 200 performed by the cloud-based application to distribute condensed subject records to user devices in association with a consult broadcast requesting assistance with treating a subject. Process 200 may be performed by cloud server 135 to enable user devices associated with different entities (e.g., hospitals) to collaborate or consult regarding treatment for a subject, while complying with data-privacy rules.

Process 200 begins at block 210 where cloud server 135 receives a set of attributes from a user device. Each attribute of the set of attributes can represent any characteristic(s) of a subject (e.g., a patient). The set of attributes may be identified by a user using an interface provided by cloud server 135. For example, the set of attributes identify demographic information of the subject and a recent symptom experienced by the subject. Non-limiting examples of demographic information include age, sex, ethnicity, state or city of residence, income range, education level, or any other suitable information. Non-limiting examples of a recent symptom include a subject currently or recently (e.g., at a last visit, at intake, within 24 hours, within a week) experienced a particular symptom (e.g., difficulty breathing, fever above a threshold temperature, blood pressures above a threshold blood pressure, etc.).

At block 220, cloud server 135 generates a record for the subject. The record may be a data element including one or more data fields. The record indicates each of the set of attributes associated with the subject. The record may be stored at a central data store, such as data registry 140 or any other cloud-based database. At block 230, cloud server 135 receives a request, which was submitted by a user using the interface. The request may be to initiate a consult broadcast. For example, the user associated with an entity is a physician at a medical center treating a subject. The user can operate a user device to access the cloud-based application to broadcast a request for assistance with treating the subject. The broadcast may be transmitted to a set of other user devices associated with a different entity.

At block 240, cloud server 135 queries the central data store using the one or more recent symptoms included in the set of attributes associated with a subject. The query results include a set of other records. Each record of the set of other records is associated with another subject. In some instances, cloud server 135 may query the central data store to identify other subject records that are similar to the subject record. Similarity may be determined by comparing the transformed representation of the entire subject record to the transformed representation of each other subject record. The comparison of the transformed representations may result in a distance (e.g., a Euclidean distance) that represents a degree of similarity between the two subject records. In other instances, similarity may be determined based on values included in a data element. For example, a target subject record may include a target data element including text that represents symptoms experienced by a subject. Each other subject record stored in the central data store may also include a data element including text that represents the symptoms of the associated subject. Cloud server 135 can transform the text included in the target data element into a numerical representation using techniques described above (e.g., a trained convolution neural network, a text vectorization technique, such as Word2Vec, etc.). The numerical representation of the text included in the target data element may be compared against the numerical representation of the text included in the matching data element of each other subject record. The result of the comparison (e.g., in a domain space, such as a Euclidean space) between two numerical representations may indicate a degree to which the text included in the target data element is similar to the text included in the data element of another subject record. At block 250, cloud server 135 identifies a set of destination addresses (e.g., other user devices associated with a different entity). Each destination address of the set of destination address is associated with a care provider for another subject associated with one or more other records of the set of other records identified at block 240. At block 260, cloud server 135 generates a condensed representation of the record for the subject. The condensed representation of the record omits, obscures, or obfuscates at least a portion of the record. The condensed representation of the record can be exchanged between external systems without violating data-privacy rules because the condensed representation of the record cannot be used to uniquely identify the subject associated with the record. Cloud server 135 can execute any masking or obfuscation techniques to generate the condensed representation of the record.

At block 270, cloud server 135 avails the condensed representation of the record with a connection input component (e.g., a selectable link, such as a hyperlink, that causes a communication channel to be established) to each destination address of the set of destination addresses. The connection input component may be a selectable element presented to each destination address. Non-limiting examples of the connection input component include a button, a link, an input element, and other suitable selectable elements. At block 280, cloud server 135 receives a communication from a destination device associated with a destination address. The communication includes an indication that the user operating the destination device selected the connection input component associated with the condensed representation of the record. At block 290, cloud server 135 establishes a communication channel between the user device and the destination device at which the connection input component was selected. The communication channel enables the user operating the user device (e.g., the physician treating the subject) to exchange messages or other data (e.g., a video feed) with the destination device associated with the destination address at which the connection input component was selected (e.g., a physician at another hospital who agreed to assist with the treatment of the patient).

In some embodiments, cloud server 135 is configured to automatically determine a location of the user device and a location of the destination device at which the connection input component was selected. Cloud server 135 can also compare the locations to determine whether to generate the condensed representation of the record. For example, at block 260, cloud server 135 may generate the condensed representation of the record because cloud server 135 determines that each destination address of the set of destination addresses is not collocated with the user device that initiated the consult broadcast. In this case, cloud server 135 may automatically determine to generate the condensed representation of the record to comply with data-privacy rules. As another example, if the set of destination addresses is associated with the same entity as the user device that initiated the consult broadcast, then cloud server 135 can transmit the record in full (e.g., without obfuscating a portion of the record) to a destination device associated with a destination address, while still complying with the data-privacy rules.

In some embodiments, cloud server 135 generates a plurality of other condensed record representations. Each of the plurality of other condensed record representations is associated with another subject. Cloud server 135 transmits the plurality of other condensed record representations to the user device; and receives, from the user device, a communication identifying selections of a subset of the plurality of other condensed record representations. Each of the set of destination addresses is represented by one of the condensed record representations. For example, generating a condensed record representation includes determining a jurisdiction of another subject associated with the condensed record representation, determining a data-privacy rule governing the exchange of subject records within the jurisdiction, and generated the condensed record representation to comply with the data-privacy rule. A first other condensed record representation of the plurality of other condensed record representations may include data of a particular type. A second other condensed record representation of the plurality of other condensed record representations may omit or obscure data of the particular type. For example, data of the particular type may be contact information, identifying information, such as name, social security number, and other suitable information that can be used to uniquely identify the other subject.

In some implementations, a communication may be received at the central data store. The communication may be transmitted by a user device operated by a user and may include an identifier of a target subject record of a target subject. The communication, when received at the central data store, may cause the central data store to query the stored set of subject records to identify an incomplete subset of the set of subject records. Each subject record of the incomplete subset may be identified and included in the incomplete subset because the subject record is determined to be similar to the target subject record along at least one dimension. Similarity between two subject records along a dimension may represent similarity with respect to a data element of the subject records, such as similarity with respect to symptoms, diagnoses, treatments, or any other suitable data elements. The one or more dimensions, along which similarity or dissimilarity is determined, may be defined automatically or may be user defined. Determining a similarity or dissimilarity between the target subject record and each subject record of the set of subject records stored in the central data store may include at least the following operations: retrieving the target subject record based on the identifier included in the communication, generating a transformed representation of the target subject record (or retrieving the existing transformed representation of the target subject record), and performing a clustering operation using the transformed representation of the target subject record and the transformed representation of each subject record of the set of subject records. The clustering operation may be performed with respect to one or more dimensions (e.g., one or more features of a subject record). For example, the clustering operation may cluster the set of subject records stored in the central data store based on the data element that contains values representing a subject's symptoms. The transformed representation of the target subject record may include a vector representation of a data element that contains values representing the subject's symptoms. The vector representation of this data element of the target subject record and the vector representations of the corresponding data element in each subject record of the set of subject records may be compared to define clusters of subject records. Each cluster of subject records may define a group of one or more subject records that share a common characteristic associated with the data element selected as the dimension of similarity. In each cluster of subject records, a Euclidean distance may be computed between the transformed representation of the target subject record and the other transformed representations of the set of subject records. A subject record may be determined to be similar to the target subject record when, for example, the Euclidean distance between the transformed representation of the subject record and the transformed representation of the target subject record is within a threshold value. Therefore, the cloud-based application and methods performed by said application enable a user to identify and optionally share subject records that are clinically relevant in relation to a query subject.

Figure 3:
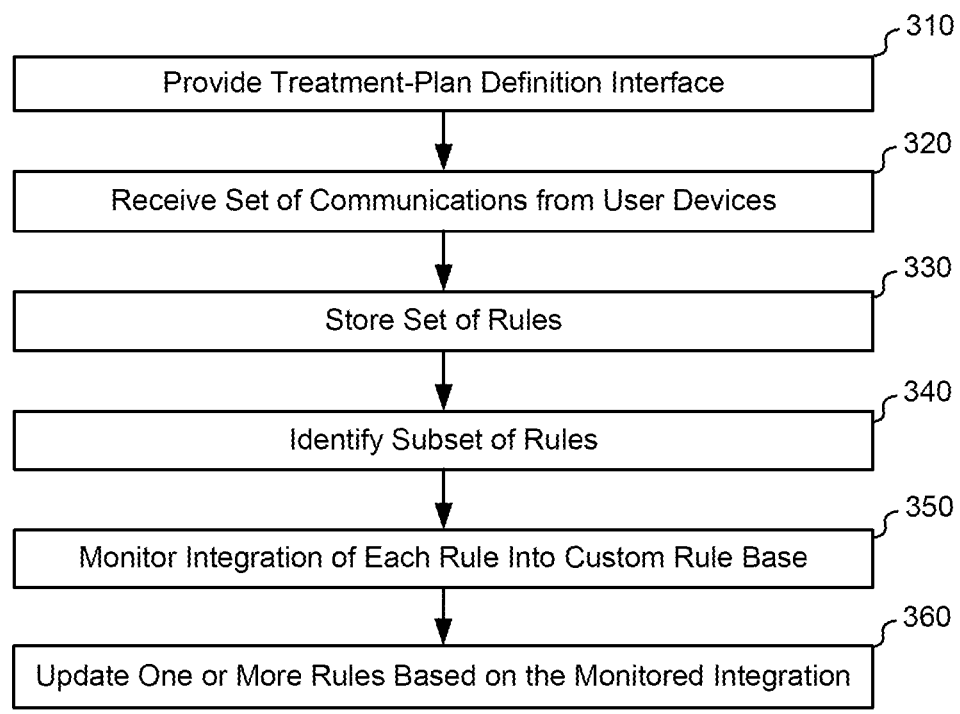
FIG. 3 is a flowchart illustrating an example of a process for monitoring the user integration of treatment-plan definitions (e.g., decision trees or treatment workflows) and automatically updating the treatment-plan definitions based on a result of the monitoring, according to some aspects of the present disclosure.

II.B. Updating Shareable Treatment-Plan Definitions Based on Aggregated User Integration FIG. 3 is a flowchart illustrating process 300 for monitoring the user integration of treatment-plan definitions (e.g., decision trees or treatment workflows) and automatically updating the treatment-plan definitions based on a result of the monitoring. Process 300 may be performed by cloud server 135 to enable a user device to define a treatment plan for treating a population of subjects with a condition. The user device may distribute the treatment-plan definition to user devices connected to internal or external networks. The user devices receiving the treatment-plan definition can determine whether to integrate the treatment-plan definition into a custom rule base. The integration into the custom rule base can be monitored and used to automatically modify the treatment-plan definition.

At block 310, cloud server 135 stores interface data that causes a treatment-plan definition interface to be displayed when a user device loads the interface data. The treatment-plan definition interface is provided to each user device of a set of user devices when the user device accesses cloud server 135 to navigate to the treatment-plan definition interface. In some embodiments, the treatment-plan definition interface enables a user to define a treatment plan for treating a population of subjects that have a condition (e.g., lymphoma).

At block 320, cloud server 135 receives a set of communications. Each communication of the set of communications is received from a user device of the set of user devices and was generated in response to an interaction between the user device and the treatment-plan definition interface. In some embodiments, the communication includes one or more criteria, for example, for defining a population of subject records. Each criteria may be represented by a variable type. For example, variable type may be a value or variable used as the condition of a criteria. The variable type of a criterion of a rule may also be any value of a condition that constrains the population of subjects to an incomplete sub-group. For example, the variable type of a rule that defines a population of pregnant women is "IF 'subject is pregnant.'" A criterion may be a filter condition for filtering a pool of subject records. For example, a criteria for defining a population of subject records associated with subjects who may develop a lymphoma may include a filter condition of "abnormality in anaplastic lymphoma kinase (ALK)" AND "over 60 years old." The communication may also include a particular type of treatment for the condition. The particular type of treatment may be associated with a certain action (e.g., undergo surgery) or refraining from certain action (e.g., reduce salt intake) that is proposed to treat the condition associated with the subjects represented by the population of subject records.

At block 330, cloud server 135 stores a set of rules in a central data store, such as data registry 140 or any other centralized server within cloud network 130. Each rule of the set of rules includes the one or more criteria and the particular treatment type included in the communication from a user device. As an illustrative example, a rule represents a treatment workflow for treating lymphoma in a subject. The rule includes the following criteria (e.g., the conditions following the "IF" statement) and a next action (e.g., the particular treatment type defined or selected by the user, and which follow the "THEN" statement): "IF 'biopsy of lymph nodes indicates lymphoma cells are present' AND 'blood test reveals lymphoma cells present' THEN 'treat with chemotherapy' AND 'active surveillance.'" Additionally, each rule of the set of rules is stored in association with an identifier corresponding to the user device from which the communication was received.

At block 340, cloud server 135 identifies a subset of the set of rules that are available across entities via the treatment-plan definition interface. A subset of rules may include the subset of the set of rules associated with a condition and that are distributed to external systems, such as other medical centers, for evaluation. For example, a rule can be selected for including in the subset of rules by evaluating a characteristic of the rule or the identifier associated with the rule. The characteristic of the rule can include a code or flag stored or appended to the stored rule. The code or flag indicates the rule is generally available to external systems (e.g., availed to entities).

At block 350, for each rule of the subset of rules identified at block 340, cloud server 135 monitors interactions with the rule. An interaction may include an external entity (e.g., external to the entity associated with the user who defined the treatment plan associated with the rule) integrating the rule into a custom rule base. For example, a user device associated with an external entity (e.g., a different hospital) evaluates the rule availed to the external entity. The evaluation includes determining whether the rule is suitable for integrating into a rule set defined by the external entity. The rule may be suitable when the user device associated with the external entity indicates that the treatment workflow that is defined using the rule is suitable to treat the condition corresponding to the rule. Continuing with the illustrative example above, the rule for treating lymphoma may be availed to an external medical center. A user associated with the external medical center determines that the rule for treating lymphoma is suitable for integrating into the rule set defined by the external medical center. Thus, after the rule is integrated into a custom rule base defined by the external medical center, other users associated with the external medical center will be able to execute the integrated rule by selecting the integrated rule from the custom rule base. Additionally, cloud server 135 monitors integration of the availed rule by detecting a signal generated or caused to be generated when the treatment-plan definition interface receives input corresponding to an integration of the rule into the custom rule base from the user device associated with the external entity.

As another illustrative example, the user device associated with the external entity uses the treatment-plan definition to integrate an interaction-specified modified version of the rule into the custom rule base. The interaction-specified modified version of the rule is a portion of the rule selected for integration into the custom rule base. Selecting a portion of the rule for integration includes selecting less than all criteria included in the rule for integration into the custom rule base. Continuing with the illustrative example above, the user device associated with the external entity selects the criteria of "IF 'biopsy of lymph nodes indicates lymphoma cells are present'" for integration into the custom rule base, but the user device does not select the criteria of "blood test reveals lymphoma cells present" for integration into the custom rule base. Thus, the interaction-specific modified version of the rule integrated into the custom rule base is "IF 'biopsy of lymph nodes indicates lymphoma cells are present' THEN 'treat with chemotherapy' AND 'active surveillance.'" The criteria of "blood test reveals lymphoma cells present" is removed from the rule to create the interaction-specified modified version of the rule, which is integrated into the custom rule base.

At block 360, cloud server 135 may detect that the interaction-specified modified version of the rule was integrated into the custom rule base defined by the external entity. Once detected, cloud server 135 may update the rule stored at the central data store of cloud network 130. The rule may be updated based on the monitored interaction(s). The term "based on" in this example corresponds to "after evaluating" or "using a result of" an evaluation of the monitored interaction(s). For example, cloud server 135 detects that the user device associated with the external entity integrated the interaction-specified modified version of the rule. In response to detecting the interaction-specified modified version of the rule, cloud server 135 may update the rule stored in the central data store from the existing rule to the interaction-specified modified version of the rule.

In some embodiments, cloud server 135 updates the rule by generating an updated version that is to be availed across external entities. Another original version may remain un-updated and is availed to a user associated with the user device from which the one or more communications that identified the criteria and particular type of treatment was received. For example, cloud server 135 updates the rule stored at the central data store, but cloud server 135 does not update another rule of the set of rules stored at the central data store.

In some embodiments, cloud server 135 may update the rule when an update condition has been satisfied. An update condition may be a threshold value. For example, the threshold value may be a number or percentage of external entities that have integrated a modified version of the rule into their custom rule bases. As another example, the update condition may be determined using an output of a trained machine-learning model. To illustrate, cloud server 135 may input the detected signals received from external entities into a multi-armed bandit model that automatically determines whether and/or when to avail the rule and/or whether and when to avail an updated version of the rule. To illustrate and only as a non-limiting example, a rule may be defined as executable code, such that the rule, upon execution, automatically queries the central data store to identify a subset of the set of subject records to further analyze. Additionally, the rule may include one or more treatment protocols for treating the subjects associated with the identified subset of subject records. The rule may be defined as a workflow for defining a subset of the set of subject records and treating the subset associated with the subset of subject records. For example, the rule may include one or more criteria for filtering subject records out of the set of subject records, and for performing certain treatment protocols on the subjects associated with the remaining subject records (e.g., the subject records remaining after the filtering has been performed on the set of subject records). While the rule is defined by a user of a first entity, the rule may be accepted (e.g., integrated into a rule base of the second entity), modified, or entirely rejected by an external user (e.g., a doctor who works at a different hospital) of a second entity (e.g., the first and second entities being two different medical facilities). In some examples, each time an external user of the second entity accepts the rule, and thus, fully integrates the rule into its codebase, then a feedback signal may be transmitted to the cloud server 135. In other examples, each time a user of the second entity modifies the rule, then a feedback signal may be transmitted to the cloud server 135. In other examples, each time a user of the second entity entirely rejects the rule, then a feedback signal may be transmitted to the cloud server 135. In each example above, the feedback signal may include data indicating the rule (e.g., a rule identifier) and whether the rule was accepted, modified, or rejected. A multi-armed bandit model (executable by cloud server 135) can be configured to intelligently select one of the original rule, the modified rule, or an entirely different rule for broadcasting to external users of other entities. The selection of the original rule, the modified rule, or the different rule may be based at least in part on the configuration of the multi-armed bandit. In some examples, the multi-armed bandit may be configured with an epsilon greedy search technique. In an epsilon greedy search technique, the multi-armed bandit model may select the original rule for broadcasting to external users of other entities with a probability of "1–epsilon," where epsilon represents a probability of exploring a new or modified rule. Thus, the multi-armed bandit model may select a modified version of the original rule or a completely new rule with a probability of the defined epsilon. The multi-armed bandit model may change the epsilon based on the feedback signals received from the other entities. For example, if the feedback signals indicate that the rule has been modified in a specific manner by different external users over a threshold number of times, then the multi-armed bandit model may learn to select the rule, as modified in the specific manner, to broadcast to external users, instead of broadcasting the original rule.

In some embodiments, cloud server 135 identifies multiple rules of the set of rules that include criteria corresponding to the same variable type and that identify same or similar types of treatment. A variable type may be a value or variable used as the condition of a criteria. The variable type of a criterion of a rule may also be any value of a condition that constrains the population of subjects to a sub-group. For example, the variable type of a rule that defines a population of pregnant women is "IF 'subject is pregnant.'" Cloud server 135 determines a new rule that is a condensed representation of the multiple rules, when the new rule is generally transmitted to the servers operated by other entities.

In some embodiments, cloud server 135 provides another interface configured to receive a set of attributes of a subject. For example, a user operating a user device to access the other interface and select a subject record that includes a set of attributes using the other interface. The selection of the subject record may cause the cloud server 135 to receive the set of attributes of the subject. Cloud server 135 identifies (e.g., determines) a particular rule for which the criteria are satisfied based on the set of attributes of the subject. For example, the evaluates the set of attributes of the subject record against the criteria of the rules stored in the central data store. To illustrate, if the set of attributes includes a data field containing the value "pregnant," and if a rule includes a single criteria of "IF 'subject is pregnant,'" then cloud server 135 identifies this rule. Cloud server 135 updates the other interface to present the particular rule and each particular type of treatment associated with the particular rule.

In some embodiments, a criterion of a rule is a variable type that relates to a particular demographic variable and/or a particular symptom-type variable. Non-limiting examples of a demographic variable include any item of information that characterizes a demographic of the subject, such as age, sex, ethnicity, race, income level, education level, location, and other suitable items of demographic information. Non-limiting examples of a symptom-type variable indicate whether a subject currently or recently (e.g., at a last visit, at intake, within 24 hours, within a week) experienced a particular symptom (e.g., difficulty breathing, fainting, fever above a threshold temperature, blood pressures above a threshold blood pressure, etc.).

In some embodiments, cloud server 135 monitors data in a registry of subject records, such as the subject records stored in data registry 140. Cloud server 135 monitors the data in the registry of subject records for each rule of the subset of rules (identified at block 340). Cloud server 135 identifies a set of subjects for which the criteria of the rule were satisfied, and for which the particular treatment was previously prescribed to the subject. Cloud server 135 identifies, for each of the set of subjects, a reported state of the subject as indicated from or using assessment or testing. For example, the reported state is any information characterizing a state of the subject in an aspect, such as whether the subject has been discharged, whether the subject is alive, measurements of the subject's blood pressure, the number of times the subject wakes up during a sleep stage, and other suitable states. Cloud server 135 determines an estimated responsiveness metric of the set of subjects to the particular treatment based on the reported states. For example, if the particular treatment of a rule is to prescribe a medication, the estimated responsiveness metric is a representation of the extent to which the medication addressed a symptom or condition experienced by the subject. As a non-limiting example, the estimated responsiveness metric of the set of subjects may be an average, weighted average, or any summation of a score assigned to each subject of the set of subjects. The score can represent or measure the effectiveness of the subject's responsiveness to the treatment. In some instances, cloud server 135 may generate the score that represents the effectiveness of the subject's responsiveness to the treatment by using a clustering technique. To illustrate and as only a non-limiting example, a set of subject records may represent subjects who previously underwent a particular treatment protocol for treating a condition. Each subject record of the set of subject record may be labeled (e.g., by a user) as having one of a positive responsiveness to the particular treatment protocol, a neutral responsiveness to the particular treatment protocol, or a negative responsiveness to the particular treatment protocol. The set of subject records may then be divided into three subsets (e.g., clusters); a first subset of subject records may correspond to subjects who had a positive responsiveness to the particular treatment protocol, a second subset of subject records may correspond to subjects who had a neutral responsiveness to the particular treatment protocol, and a third subset of subject records may correspond to subjects who had a neutral responsiveness to the particular treatment protocol. Cloud server 135 may transform each subject record of the first subset of subject records into a transformed representation, according to implementations described above. Cloud server 135 may also transform each subject record of the second subset of subject records into a transformed representation, using techniques described above. Lastly, cloud server 135 may transform each subject record of the third subject of subject records into a transformed representation, using the techniques described above. In some implementations, determining a predicted responsiveness of a new subject to the particular treatment protocol may include transforming the new subject record of the new subject into a new transformed representation. The new transformed representation may be compared in a domain space (e.g., a Euclidean space) with the transformed representations of each cluster or subset of subject records. If the new transformed representation is closest to a representative value (e.g., the centroid) of the transformed representations associated with the first subset, then the new subject is predicted to have a positive responsiveness to the particular treatment. If the new transformed representation is closest to a representative value (e.g., the centroid) of the transformed representations of the second subset, then the new subject is predicted to have a neutral responsiveness to the particular treatment. Lastly, if the new transformed representation is closest to a representative value (e.g., the centroid) of the transformed representations of the third subset, then the new subject is predicted to have a negative responsiveness to the particular treatment protocol. A centroid may be a multidimensional average of the transformed representations associated with a subset. Cloud server 135 can cause the subset of the set of rules and the estimated responsiveness metrics of the set of subjects to be displayed or otherwise presented in the treatment-plan definition interface.

Figure 4:
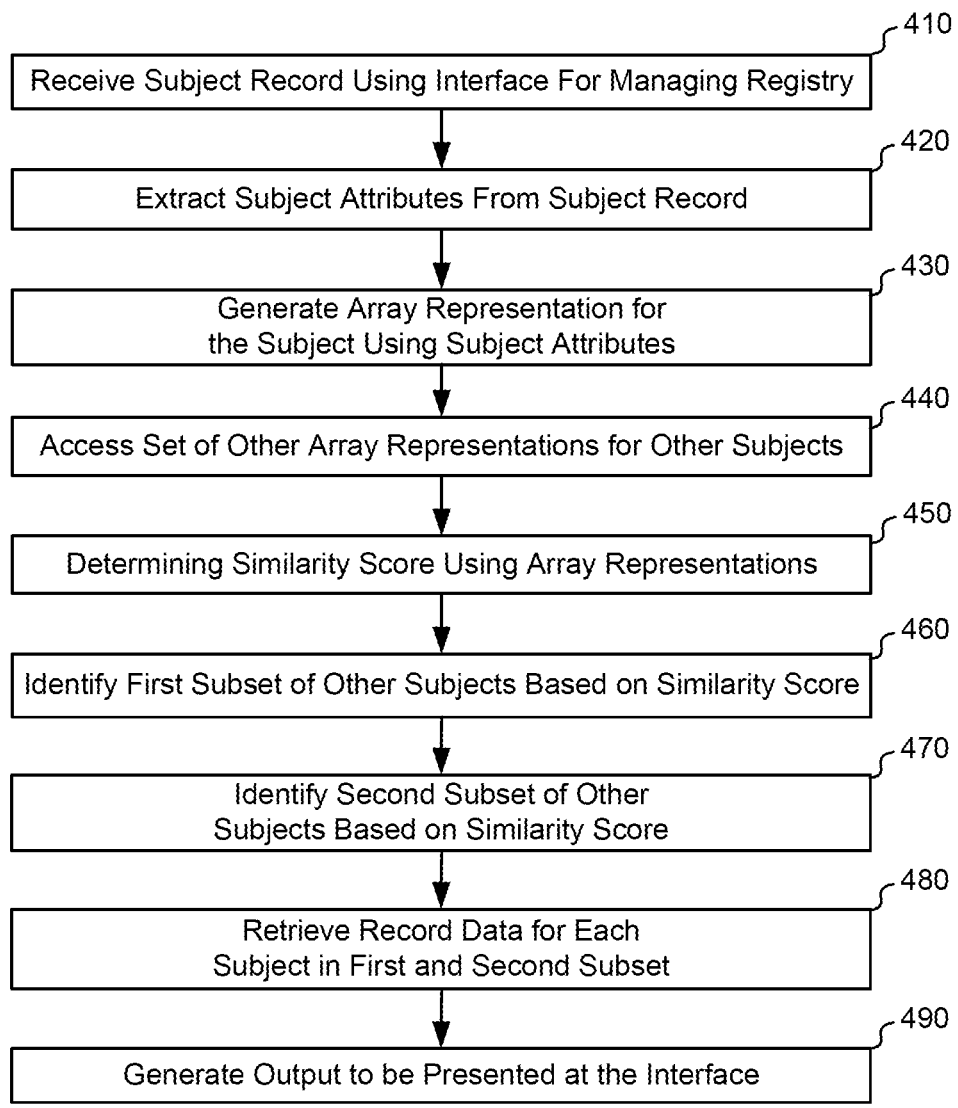
FIG. 4 is a flowchart illustrating an example of a process for recommending treatments for a subject, according to some aspects of the present disclosure.

II.C. Presenting Treatment Recommendations with Associated Efficacy Using Treatments Prescribed to Similar Subjects FIG. 4 is a flowchart illustrating process 400 for recommending treatments for a subject. Process 400 can be performed by cloud server 135 to display to a user device associated with a medical entity recommended treatments for a subject and the efficacy of each recommended treatment. The recommended treatments can be identified using a result of evaluating efficacies of treatments previously prescribed to similar subjects.

At block 410, cloud server 135 receives input corresponding to a subject record that characterizes aspects of a subject. The input is received from a user device associated with an entity. Further, the input is received in response to the user device selecting or otherwise identifying the subject record using an interface associated with an instance of a platform configured to manage a registry of subject records. User devices may access the interface by loading interface data stored at a web server (not shown) connected within cloud network 130. The web server may be included or executed on cloud server 135.

At block 420, cloud server 135 extracts a set of subject attributes from the subject record received at block 410. A subject attribute characterizes an aspect of the subject. Non-limiting examples of subject attributes include any information found in an electronic health record (e.g. a data element as described above), any demographic information, an age, a sex, an ethnicity, a recent or historical symptom, a condition, a severity of the condition, and any other suitable information that characterizes the subject.

At block 430, cloud server 135 generates an array representation of the subject record using the set of subject attributes (for example, by transforming the subject record as described above). For example, the array representation is a vector representation of the values included in the subject record. The vector representation may be a vector in a domain space, such as a Euclidean space. The array representation, however, can be any numerical representation of a value of a data element of the subject record. In some embodiments, cloud server 135 can perform feature decomposition techniques, such as singular value decomposition (SVD), to generate the values representing the set of subject attributes of the array representation of the subject record.

At block 440, cloud server 135 accesses a set of other array representations characterizing multiple other subjects. An array representation included in the set of other array representations may be a vector representation of a subject record that characterizes another subject (e.g., one of the multiple other subjects).

At block 450, cloud server 135 determines a similarity score representing a similarity between the array representation representing the subject and the array representation of each of the other subjects. For example, the similarity score is calculated using a function of a distance (in the domain space) between the array representation representing the subject and the array representation representing the other subject. To illustrate and as only a non-limiting example, the similarity score may be calculated using a range of "0" to "1," with "0" representing a distance beyond a defined threshold and "1" representing that the array representations have no distance between them. To illustrate and only as a non-limiting example, the similarity score may be based on the Euclidean distance between two array representations (e.g., vectors).

At block 460, cloud server 135 identifies a first subset of the multiple other subjects. Subjects may be included in the first subset when the similarity score associated with a subject is within a predetermined absolute or relative range. Similarly, at block 470, cloud server identifies a second subset of the multiple other subjects. However, subjects may be included in the second subset when the similarity score of this subject is within another predetermine range.

At block 480, cloud server 135 retrieves record data for each subject in the first subset and in the second subset of the multiple other subjects. The record data include the attributes that are included in a subject record characterizing a subject. For example, the subject record data identifies a treatment received by the subject and the subject's responsiveness to the treatment. The responsiveness to the treatment may be represented by text (e.g., "subject responded positively to treatment") or a score indicating an extent to which the subject responded positively or negatively to the treatment (e.g., a score from "0" to "1" with "0" indicating a negative responsiveness and "1" indicating a positive responsiveness). In some instances, a treatment responsiveness may indicate a degree to which a subject responded positively to a treatment that was previously performed on the subject. For example, the treatment responsiveness may be a numerical (e.g., a score from "0" to "10") or non-numerical value (e.g., a word assigned to represent the responsiveness, such as "positive," "neutral," or "negative"). In some examples, the treatment responsiveness for previously treated subjects may be user defined. In other examples, the treatment responsiveness may be determined automatically based on a result of a test or a measurement taken from the user. For example, the treatment responsiveness may be determined automatically based on values included in a blood test performed on the subject.

At block 490, cloud server 135 generates an output to be presented at the interface on the user device. The output may indicate, for example, a recommendation of one or more treatments for the subject. The recommendation of one or more treatments may be determined based on, for example, the treatments received by the other subjects in the first and second subsets, the treatment responsiveness of subjects in the first and second subsets, and the differences between the subject attributes of subjects in the second subset and subject attributes of the subject.

In some embodiments, cloud server 135 determines that the subject and one of the subjects from the first or second subset are being treated or were treated by the same medical entities. Cloud server 135 determines that the subject and another subject of the first or second subset are being treated or were treated by different medical entities. Cloud server 135 may avail differentially obfuscated versions of records of the subjects via the interface. The cloud-based application can automatically provide differently obfuscated versions of records to entities based on varying constraints imposed on data sharing by the data-privacy rules of different jurisdictions. In some embodiments, cloud server 135 identifies the first subset and the second subset of subject records by performing a clustering operation on the transformed representations of a set of subject records.

II.D. Automatically Obfuscating Query Results from External Entities

Figure 5:
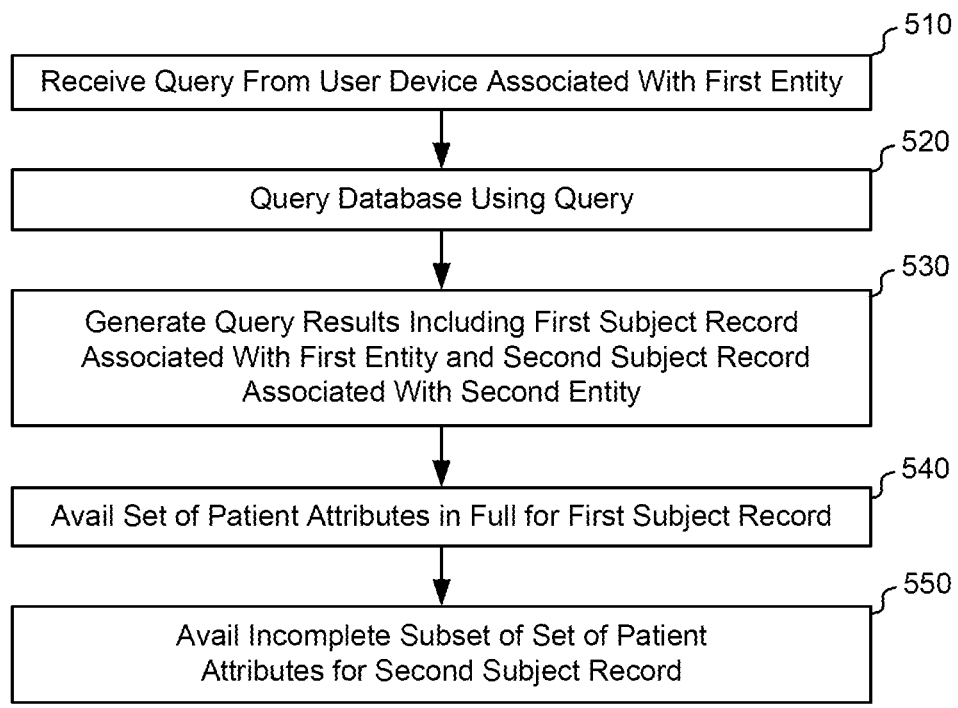
FIG. 5 is a flowchart illustrating an example of a process for obfuscating query results to comply with data-privacy rules, according to some aspects of the present disclosure.

FIG. 5 is a flowchart illustrating process 500 for obfuscating query results to comply with data-privacy rules. Process 500 may be performed by cloud server 135 as an executing rule that ensures data sharing of subject records with external entities complies with data-privacy rules. The cloud-based application may enable a user device to query data registry 140 for subject records that satisfy a query constraint. The query results, however, may include data records originating from external entities. Thus, process 500 enables cloud server 135 to provide user devices with additional information on treatments from external entities, while complying with data-privacy rules.

At block 510, cloud server 135 receives a query from a user device associated with a first entity. For example, the first entity is a medical center associated with a first set of subject records. The query may include a set of symptoms associated with a medical condition or any other information constraining a query search of data registry 140.

At block 520, cloud server 135 queries a database using the query received from the user device. At block 530, cloud server 135 generates a data set of query results that correspond to the set of symptoms and are associated with the medical conditions. A query result that corresponds to a set of symptoms may include subject records including at least one of the set of symptoms. For example, the user device transmits a query for subject records of subjects who have been diagnosed with lymphoma. The query results include at least one subject record from the first set of subject records (which originate or were created at the first entity) and at least one subject record from a second set of subject records associated with a second entity (e.g., a medical center different from the first entity). Each of the subject record from the first set of subject records and the subject record from the second set of subject records may include a set of subject attributes. A subject attribute can characterize any aspect of a subject.

At block 540, cloud server 135 presents (e.g., avails or otherwise makes available) to the user device the set of subject attributes in full for subject records included in the first set of subject records because these records originate from the first entity. Presenting a subject record in full includes making the set of attributes included in a subject record available to the user device for evaluation or interaction using the interface. At block 550, cloud server 135 also or alternatively avails to the user device an incomplete subset of the set of subject attributes for each subject record included in the second set of subject records. Providing an incomplete subset of the set of subject attribute provides anonymity to subjects because the incomplete subset of subject attributes cannot be used to uniquely identify a subject. For example, providing an incomplete subset may include available four of 10 subject attributes to anonymize the subject associated with the 10 subject attributes. In some embodiments, at block 550, cloud server 135 avails an obfuscated set of subject attributes for each subject record included in the second subject. Obfuscating the set of attributes include reducing the granularity of information provided. For example, instead of availing the subject attribute of a subject's address, the obfuscated attribute may be a zip code or a state in which the subject lives. Whether an incomplete subject or an obfuscated subset is availed, cloud server 135 anonymizes a subject associated with the subject record.

II.E. Chatbot Integration with Self-Learning Knowledge Base

Figure 6:
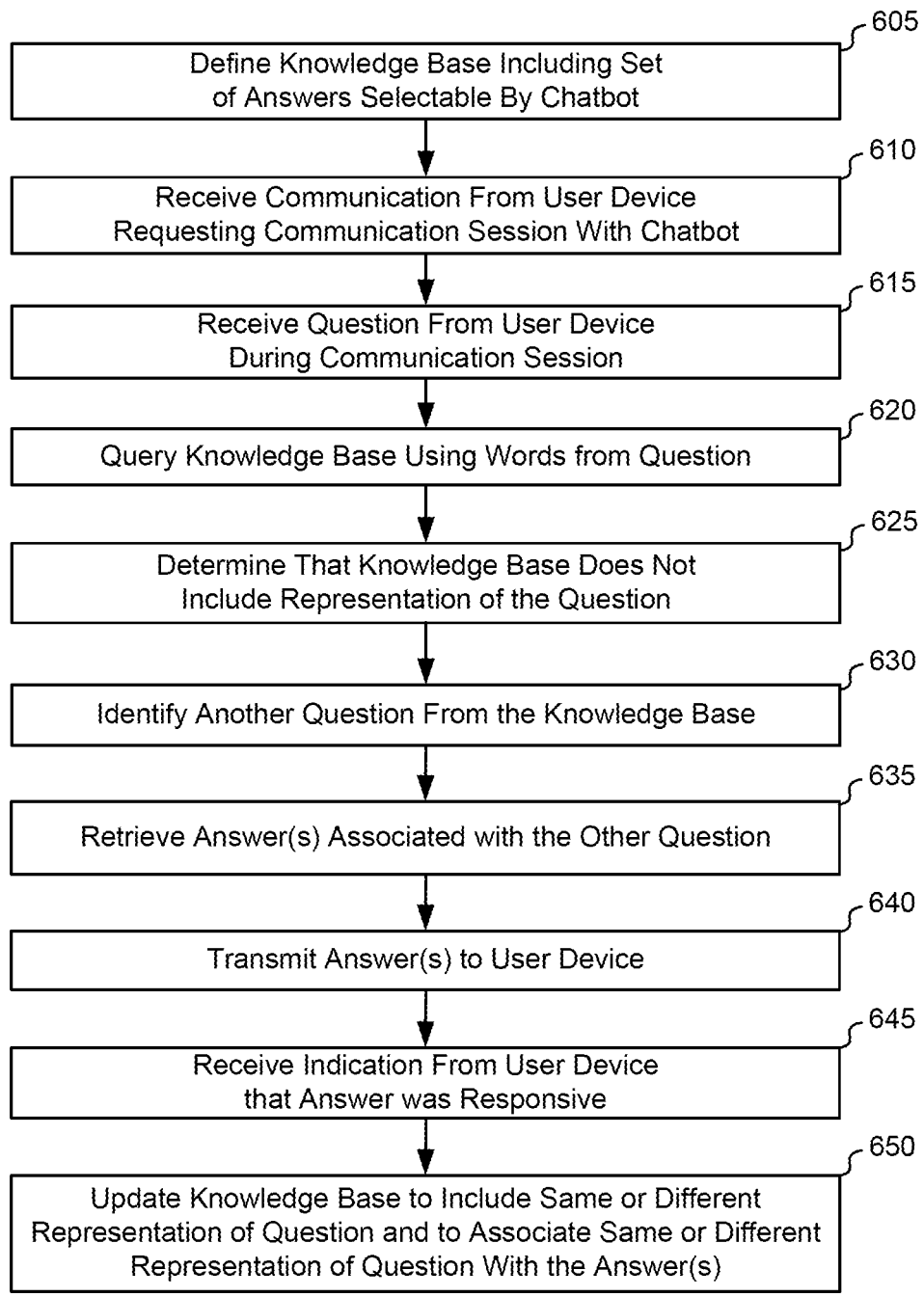
FIG. 6 is a flowchart illustrating an example of a process for communicating with users using bot scripts, such as a chatbot, according to some aspects of the present disclosure.

FIG. 6 is a flowchart illustrating process 600 for communicating with users using bot scripts, such as a chatbot. Process 600 may be performed by cloud server 135 for automatically linking new questions provided by users to existing questions in a knowledge base to provide a response to the new question. A chatbot may be configured to provide answers to questions associated with a condition. For example, the questions may relate to the identification of a diagnosis, prognosis and/or treatment for a subject. As such, the process explained below may be implemented as part of a computer implemented method of diagnosing a condition associated with a subject, a computer implemented method of identifying a treatment or treatment plan for a subject, or a computer implemented method of providing a prognosis for a subject.

At block 605, cloud server 135 defines a knowledge base, which includes a set of answers. The knowledge base may be a data structure stored in memory. The data structure stores text representing the set of answers to defined questions. Each answer may be selectable by a chatbot in response to a question received from a user device during a communication session. The knowledge base may be automatically defined (e.g., by retrieving text from a data source and parsing through the text using natural language processing techniques) or user defined (e.g., by a researcher or physician).

At block 610, cloud server 135 receives a communication from a particular user device. The communication corresponds to a request to initiate a communication session with a particular chatbot. For example, a physician or subject may operate a user device to communicate with a chatbot in a chat session. Cloud server 135 (or a module stored within cloud server 135) may manage or establish communication sessions between user devices and chatbots. At block 615, cloud server 135 receives a particular question from the particular user device during the communication session. The question can be a string of text that is processed using natural language processing techniques.

At block 620, cloud server 135 queries the knowledge base using at least some words extracted from the particular question. The words may be extracted from the string of text representing the particular question using natural language processing techniques. At block 625, cloud server 135 determines that the knowledge base does not include a representation of the particular question. In this case, the question received may be newly posed to a chatbot. At block 630, cloud server 135 identifies another question representation from the knowledge base. Cloud server 135 may identify another question representation by comparing the question received from the user device to the other question representations stored in the knowledge base. If a similarity is determined, for example, based on an analysis of the question representations using natural language processing techniques, then cloud server 135 identifies the other question representation.

At block 635, cloud server 135 retrieves an answer of the set of answers associated, in the knowledge base, with the other question representation. At block 640, the answer retrieved at block 635 is transmitted to the particular user device as an answer to the question received, even though the knowledge based did not include a representation of the question received. At block 645, cloud server 135 receives an indication from the particular user device. For example, the indication may be received in response to the user device indicating that the answer provided by the chatbot was responsive to the particular question.

At block 650, cloud server 135 updates the knowledge base to include the representation of the particular question or different representation of the particular question. For example, storing a representation of a question includes storing keywords included in the question in a data structure. Cloud server 135 may also associate the same or different representation of the particular question with the more answer transmitted to the particular user device.

In some embodiments, cloud server 135 accesses a subject record associated with the particular user device. Cloud server 135 determines a plurality of answers to the particular question. Cloud server 135 then selects an answer from the set of answers. The selection of the answer, however, is based at least in part on one or more values included in the subject record associated with the particular user device. For example, a value included in the subject record may represent a symptom recently experienced by the subject. The chatbot may be configured to select an answer that is dependent on the symptom recently experienced by the subject. In some instances, cloud server 135 may access a learn-to-rank machine-learning model that has been trained to predict an order for each answer in a set of answers. The learn-to-rank machine-learning model may be trained using a training set of answers. Each answer of the training set of answers may be labeled with one or more symptoms and a relevance score for that symptom. The relevance score may represent a relevance of the associated answer to a given symptom of the one or more symptoms. The relevance score may be user defined or automatically determined based on certain factors, such as frequency of a word (e.g., the word(s) for the symptom) in a training answer. The training set of answers may be different from the set of answers used when the chatbot is operational in a production environment. The learn-to-rank machine-learning model may learn how to order the set of answers (used in the production environment) in terms of relevance to a symptom (which is detected from the subject profile) based on the patterns learned by the learn-to-rank model (e.g., the patterns between the labeled training set of answers and the associated relevance scores for each symptom of one or more symptoms). The chatbot may select an answer from the set of answers used in the production environment based on the predicted ordering of the set of answers. In some instances, each answer of the set of answers may be associated with a tag or code indicating one or more symptoms that are associated with the answer. Cloud server 135 may compare the value that represents the symptom recently experienced by the subject with the tag or code associated with each answer.

III. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implemented method of performing a clinical assessment for a subject comprising:
   receiving, at a computing system and from a user device, a set of attributes of the subject as identified by a user using an interface, the set of attributes characterizing the subject and one or more symptoms of the subject;
   generating a record for the subject, the record indicating each of the set of attributes, the record including a data element containing a non-numerical value that represents a symptom of the one or more symptoms;
   transforming the non-numerical value that represents the symptom into a transformed representation, the transformed representation numerically representing the non-numerical value, wherein the data element comprises image data, the transforming the non-numerical value comprises transforming the image data into the transformed representation and is performed using a trained auto-encoder neural network which is trained to generate latent-space representations from input images, and the trained auto-encoder neural network extracts at least a subset of salient features from a set of features detected within the image data;
   after the transforming, storing the record including the transformed representation in a central data store;
   receiving a request submitted via the interface to initiate a consult broadcast;
   querying the central data store using the transformed representation, wherein querying includes comparing the transformed representation of the non-numerical value with another transformed representation of another non-numerical value contained in another data element of another record;
   identifying a set of other records based on a result of the comparison;
   identifying a set of destination addresses, each of the set of destination addresses being associated with a care provider for another subject associated with one or more of the set of other records;
   generating a condensed representation of the record for the subject that omits or obscures at least one of the set of attributes;
   transmitting the condensed representation of the record with a selectable element to each of the set of destination addresses;
   receiving, from another device corresponding to the destination address from the set of destination addresses, a communication generated upon the another device selecting the selectable element; and
   establishing a communication channel between the user device and the other device.

2. The computer-implemented method of claim 1, wherein performing the clinical assessment comprises one or more of: identifying a treatment for the subject, identifying a condition associated with the subject, determining a prognosis for the subject, wherein the identifying and/or determining is based on the set of other records, and/or wherein the user device and the other device are associated with different medical-care institutions.

3. The computer-implemented method of claim 1, wherein transforming the non-numerical value that represents the symptom into the transformed representation further comprises:
   identifying one or more words from the non-numerical value that represents the symptom of the one or more symptoms;
   inputting each word of the one or more words into a word-to-vector machine learning model; and
   generating, based on an output of the word-to-vector machine learning model, the transformed representation, the transformed representation being an N-dimensional vector that characterizes each word of the one or more words.

4. The computer-implemented method of claim 1, wherein the comparing of the transformed representation of the non-numerical value with another transformed representation of another non-numerical value further comprises:
   determining a distance between the transformed representation and the other transformed representation in a domain space, the distance representing an extent to which the record and the other record are similar.

5. The computer-implemented method of claim 4, wherein the domain space is a Euclidean space.

6. The computer-implemented method of claim 4, wherein, when the distance between the transformed representation and the other transformed representation is within a threshold, the record and the other record are determined to be similar.

7. The computer-implemented method of claim 1, further comprising:
   generating a plurality of other condensed record representations, including, for each of the plurality of other condensed record representations:
      determining a jurisdiction that corresponds to another subject corresponding to the other condensed record representation;
      determining one or more other data-privacy rules associated with the jurisdiction; and
      generating the other condensed record representation based on the one or more other data-privacy rules, wherein a first other condensed record representation of the plurality of other condensed record representations includes data of a particular type, and wherein a second other condensed record representation of the plurality of other condensed record representations omits or obscures data of the particular type.

8. The computer-implemented method of claim 1, wherein querying the central data store further comprises:
   determining, for each other record of a plurality of other records, a score characterizing a similarity between at least part of the other record and at least part of the record for the subject, the similarity being determined based on a distance between the transformed representation and the transformed representation of each other record of the plurality of other records in a domain space; and defining the set of other records to be a subset of the plurality of other records associated for which the scores are within a threshold.

9. The computer-implemented method of claim 1, further comprising:

identifying another data element of a set of data elements included in the record, the other data element containing image data representing an image associated with the subject;

inputting the image data into the trained auto-encoder neural network; and generating, based on an output of the trained auto-encoder neural network, a reduced-dimensionality version of the image data, the reduced-dimensionality version of the image data being used as the transformed representation of the image data.

10. The computer-implemented method of claim 1, further comprising:

identifying another data element of the set of data elements included in the record, the other data element containing time-variant information representing a series of events associated with the subject; and transforming the time-variant information into the transformed representation.

11. The computer-implemented method of claim 10, further comprising:

generating a combined transformed representation that characterizes the set of data elements included in the record by combining the transformed representation of the non-numerical value, a transformed representation of the image data, and a transformed representation of the time-variant information.

12. The computer-implemented method of claim 11, further comprising:

identifying a similar record from the set of other records, the similar record being identified based on a comparison between the combined transformed representation characterizing the record with another transformed representation that characterizes another record.

13. The computer-implemented method of claim 1, wherein the querying of the central data store further uses at least a portion of demographic information to identify the set of other records.

14. The computer-implemented method of claim 1, wherein the communication channel is a secure chatroom.

15. A system comprising:

one or more processors; and a non-transitory computer-readable storage medium containing instructions which, when executed on the one or more processors, cause the one or more processors to perform operations including:

receiving, at a computing system and from a user device, a set of attributes of the subject as identified by a user using an interface, the set of attributes characterizing the subject and one or more symptoms of the subject;

generating a record for the subject, the record indicating each of the set of attributes, the record including a data element containing a non-numerical value that represents a symptom of the one or more symptoms;

transforming the non-numerical value that represents the symptom into a transformed representation, the transformed representation numerically representing the non-numerical value, wherein the data element comprises image data, the transforming the non-numerical value comprises transforming the image data into the transformed representation and is performed using a trained auto-encoder neural network which is trained to generate latent-space representations from input images, and the trained auto-encoder neural network extracts at least a subset of salient features from a set of features detected within the image data;

after the transforming, storing the record including the transformed representation in a central data store;

receiving a request submitted via the interface to initiate a consult broadcast;

querying the central data store using the transformed representation, wherein querying includes comparing the transformed representation of the non-numerical value with another transformed representation of another non-numerical value contained in another data element of another record;

identifying a set of other records based on a result of the comparison;

identifying a set of destination addresses, each of the set of destination addresses being associated with a care provider for another subject associated with one or more of the set of other records;

generating a condensed representation of the record for the subject that omits or obscures at least one of the set of attributes;

transmitting the condensed representation of the record with a selectable element to each of the set of destination addresses;

receiving, from another device corresponding to the destination address from the set of destination addresses, a communication generated upon the another device selecting the selectable element; and establishing a communication channel between the user device and the other device.

* * * * *